(12) United States Patent
Swaminathan et al.

(10) Patent No.: US 9,844,663 B2
(45) Date of Patent: Dec. 19, 2017

(54) DEVICE AND METHOD FOR POSITIONING AN ELECTRODE IN TISSUE

(71) Applicant: THE BOARD OF TRUSTEES OF THE LELAND STANFORD JUNIOR UNIVERSITY, Palo Alto, CA (US)

(72) Inventors: Aravind Swaminathan, San Mateo, CA (US); Ellis Garai, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 14/708,792

(22) Filed: May 11, 2015

(65) Prior Publication Data
US 2015/0343201 A1 Dec. 3, 2015

Related U.S. Application Data

(63) Continuation of application No. 13/219,874, filed on Aug. 29, 2011.
(Continued)

(51) Int. Cl.
*A61B 19/00* (2006.01)
*A61N 1/05* (2006.01)

(52) U.S. Cl.
CPC ............ *A61N 1/057* (2013.01); *A61N 1/0558* (2013.01); *A61N 1/0573* (2013.01)

(58) Field of Classification Search
CPC .... A61N 1/0558; A61N 1/057; A61N 1/0573; A61N 1/0587; A61N 1/059;
(Continued)

(56) References Cited

U.S. PATENT DOCUMENTS 4,570,642 A * 2/1986 Kane .................... A61N 1/0573
607/127
5,255,693 A 10/1993 Dutcher et al.
(Continued)

FOREIGN PATENT DOCUMENTS

JP 2002-542891 12/2002
JP 2004-510507 4/2004
(Continued)

OTHER PUBLICATIONS

First Office Action issued by the Japanese Patent Office for corresponding Japanese Patent Application No. 2013-230158, dated Jun. 1, 2015, pp. 1-5.
(Continued)

*Primary Examiner* — Diane Yabut
*Assistant Examiner* — Martin T Ton
(74) *Attorney, Agent, or Firm* — Merchant & Gould P.C.

(57) ABSTRACT

A device for positioning an electrode in tissue includes: a lead body having a distal portion; an electrode array coupled to the lead distal portion; an anchoring element having an anchor tip and being operable in a first configuration in which the anchor tip is retracted within the lead and in a second configuration in which the anchor tip is extended outside the lead and configured to fixate within the tissue; and a displacement mechanism that is actuated to bias the electrode array or the anchoring element toward the tissue. A method for positioning an electrode in tissue includes: navigating, to the tissue, a lead with an electrode array, an anchoring element with a distal anchor tip, and a displacement mechanism; biasing the electrode array and anchoring element towards the tissue with the displacement mechanism; and deploying the anchoring element, and verifying fixation of the anchor tip within the tissue.

13 Claims, 15 Drawing Sheets

Related U.S. Application Data

(60) Provisional application No. 61/501,450, filed on Jun. 27, 2011, provisional application No. 61/445,992, filed on Feb. 23, 2011, provisional application No. 61/427,306, filed on Dec. 27, 2010, provisional application No. 61/420,060, filed on Dec. 6, 2010, provisional application No. 61/412,992, filed on Nov. 12, 2010, provisional application No. 61/387,185, filed on Sep. 28, 2010.

(58) Field of Classification Search
CPC .......... A61N 1/0592; A61N 2001/0578; A61B 5/6682; A61B 17/0644; A61B 2018/00273
See application file for complete search history.

(56) References Cited

U.S. PATENT DOCUMENTS

| | | | |
|---|---|---|---|
| 5,336,252 A | 8/1994 | Cohen | |
| 5,443,492 A | 8/1995 | Stokes et al. | |
| 5,476,500 A * | 12/1995 | Fain | A61N 1/0573 600/375 |
| 5,571,162 A | 11/1996 | Lin | |
| 5,683,447 A | 11/1997 | Bush et al. | |
| 5,871,531 A | 2/1999 | Struble | |
| 6,055,457 A | 4/2000 | Bonner | |
| 6,942,613 B2 | 9/2005 | Ewers et al. | |
| 7,056,286 B2 | 6/2006 | Ravenscroft et al. | |
| 7,099,718 B1 | 8/2006 | Thacker | |
| 7,211,063 B2 | 5/2007 | Tom | |
| 7,231,260 B2 | 6/2007 | Wallace et al. | |
| 7,274,965 B1 | 9/2007 | Karicherla et al. | |
| 7,526,342 B2 * | 4/2009 | Chin | A61B 17/00008 607/119 |
| 7,546,166 B2 | 6/2009 | Michels et al. | |
| 7,662,151 B2 | 2/2010 | Crompton, Jr. et al. | |
| 7,684,873 B2 | 3/2010 | Gerber | |
| 7,736,198 B2 | 6/2010 | Bjorklund et al. | |
| 7,765,012 B2 | 7/2010 | Gerber | |
| 7,765,015 B2 | 7/2010 | Johnson et al. | |
| 7,865,249 B2 | 1/2011 | Reddy | |
| 7,991,484 B1 * | 8/2011 | Sengupta | A61N 1/3702 607/126 |
| 8,019,440 B2 | 9/2011 | Kokones et al. | |
| 8,055,356 B2 | 11/2011 | Wengreen et al. | |
| 8,398,672 B2 | 3/2013 | Kleshinski et al. | |
| 8,409,239 B2 | 4/2013 | Kleshinski et al. | |
| 2003/0149331 A1 * | 8/2003 | Geitz | A61N 5/1001 600/4 |
| 2003/0212446 A1 * | 11/2003 | Kaplan | A61N 1/0587 607/129 |
| 2004/0158143 A1 * | 8/2004 | Flaherty | A61B 1/3137 600/407 |
| 2005/0251238 A1 | 11/2005 | Wallace et al. | |
| 2007/0051377 A1 | 3/2007 | Douk | |
| 2007/0208357 A1 | 9/2007 | Houser et al. | |
| 2007/0213798 A1 | 9/2007 | Dreier et al. | |
| 2008/0051832 A1 | 2/2008 | To et al. | |
| 2008/0051847 A1 | 2/2008 | Kelly | |
| 2008/0077217 A1 * | 3/2008 | Santamore | A61N 1/056 607/120 |
| 2008/0103575 A1 | 5/2008 | Gerber | |
| 2008/0109054 A1 | 5/2008 | Hastings et al. | |
| 2009/0012592 A1 | 1/2009 | Buysman et al. | |
| 2009/0030331 A1 | 1/2009 | Hochareon et al. | |
| 2009/0076476 A1 | 3/2009 | Barbagli et al. | |
| 2009/0248095 A1 | 10/2009 | Schleicher | |
| 2009/0259272 A1 | 10/2009 | Reddy et al. | |
| 2010/0198041 A1 | 8/2010 | Christian et al. | |
| 2010/0204560 A1 | 8/2010 | Salahieh et al. | |
| 2012/0123531 A1 * | 5/2012 | Tsukashima | A61F 2/2448 623/2.37 |

FOREIGN PATENT DOCUMENTS

| | | |
|---|---|---|
| WO | 00/66052 | 11/2000 |
| WO | 2009135080 | 11/2009 |
| WO | 2012/028475 | 3/2012 |
| WO | 2012047408 A1 | 4/2012 |

OTHER PUBLICATIONS

Final Rejection issued for Japanese Patent Application No. 2013-530158, dated Feb. 8, 2016, English Translation (4 pages).
First Examination Report for European Patent Application No. 11831130.7, dated May 2, 2016 (4 pages).
International Search Report and Written Opinion for PCT/US2011/049499, dated Jan. 6, 2012, 9 pages.
European Search Report for Application No. 11831130.7, dated Apr. 3, 2014, 7 pages.
Japanese Final Rejection issued for Japanese Patent Application No. 2013-530158, dated Feb. 10, 2016, 4 pages.

* cited by examiner

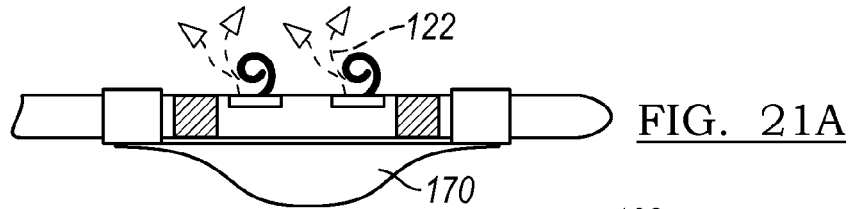
FIG. 21A
FIG. 21B
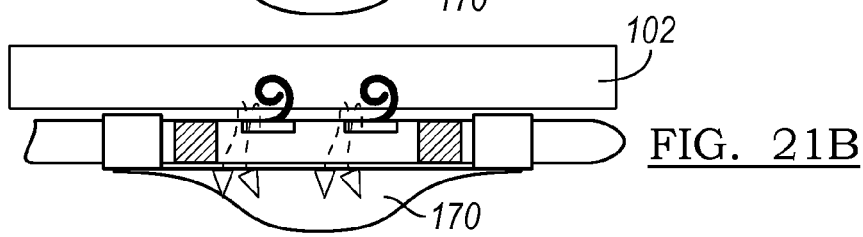
FIG. 22A
FIG. 22B
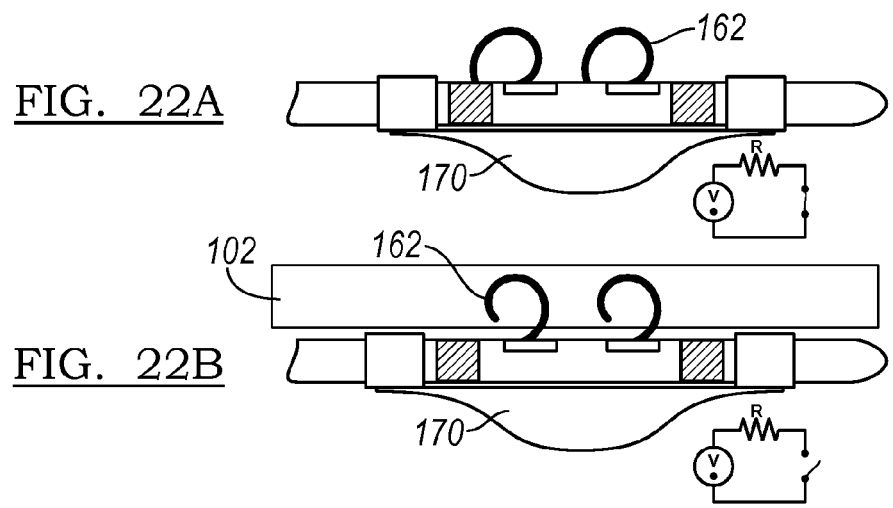
FIG. 23
FIG. 24

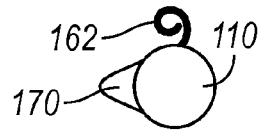 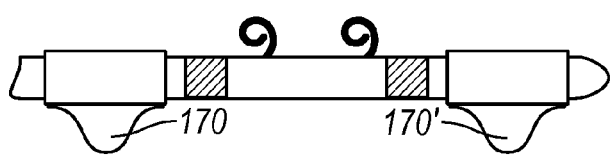
FIG. 25A  FIG. 25B

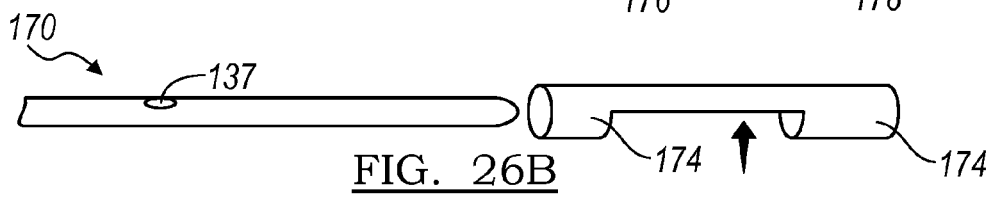
FIG. 26B
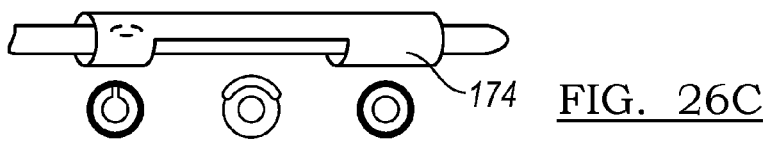
FIG. 26C
FIG. 26D
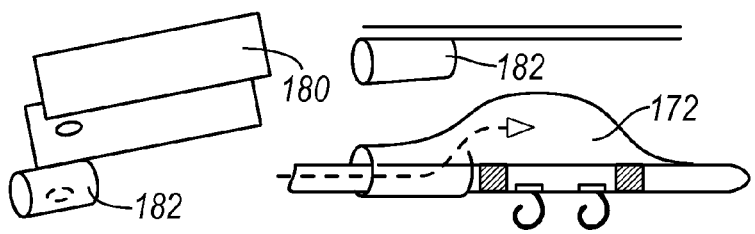
FIG. 27A
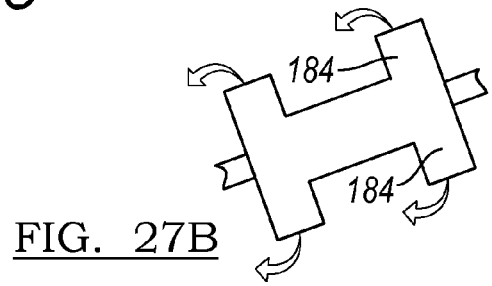
FIG. 27B

DEVICE AND METHOD FOR POSITIONING AN ELECTRODE IN TISSUE

CROSS-REFERENCE TO RELATED APPLICATION(S)

This application is a continuation of U.S. patent application Ser. No. 13/219,874, entitled "Device and Method for Positioning an Electrode in Tissue," filed Aug. 29, 2011 and claims priority to U.S. Provisional Patent Application No. 61/501,450, entitled "Pacing Device," filed on Jun. 27, 2011; U.S. Provisional Patent Application No. 61/445,992, entitled "Pacing Device," filed on Feb. 23, 2011; U.S. Provisional Patent Application No. 61/427,306, entitled "Rhythm Support Device 5," filed on Dec. 27, 2010; U.S. Provisional Patent Application No. 61/420,060, entitled "Pacing Device," filed on Dec. 6, 2010; U.S. Provisional Patent Application No. 61/412,992, entitled "Pacing Device," filed on Nov. 12, 2010 and U.S. Provisional Patent Application No. 61/387,185, entitled "Rhythm Support Device II," filed on Sep. 28, 2010. The full disclosure of the above-listed patent application is hereby incorporated by reference herein.

GOVERNMENT LICENSE RIGHTS

This invention was made with Government support under contract RR025744 awarded by the National Institutes of Health. The Government has certain rights in the invention.

TECHNICAL FIELD

This invention relates generally to the electrode stimulation device field, and more specifically to a new and useful system and method for positioning an electrode in tissue in the electrode stimulation device field.

BACKGROUND

Bradycardia (reduced heart rate) is a common condition affecting millions of patients annually. Although many such patients require implantation of permanent pacemaker devices to help regulate heart rate, other patients experience bradycardia with reversible causes that do not require permanent pacemaker implantation and may instead receive temporary bradycardia support, such as over a period of less than one week. One common treatment for temporary bradycardia support involves a system including transvenous electrode pacing leads that are inserted directly into the right ventricle of the heart to stimulate and regulate cardiac function. However, the conventional versions of these systems have several drawbacks.

Thus, there is a need in the electrode stimulation device field to create a new and useful device and method for positioning an electrode in tissue in the electrode stimulation device field. This invention provides a new and useful device and method for positioning an electrode in tissue.

These and other aspects and embodiments will be described in further detail below, in reference to the attached drawing figures.

BRIEF DESCRIPTION OF DRAWINGS

FIGS. 21A and 21B are variations of verifying anchoring element fixation and electrode array position in the system of a preferred embodiment;

FIGS. 22A and 22B are variations of verifying anchoring element fixation and electrode array position in the system of a preferred embodiment;

FIGS. 23 and 24 are variations of verifying anchoring element fixation and electrode array position in the system of a preferred embodiment;

FIGS. 25A and 25B are schematics of variations of the displacement mechanism arrangement in the system of a preferred embodiment;

FIGS. 26A-26D are preferred and alternative variations of assembling the displacement mechanism;

FIGS. 27A and 27B are preferred and alternative variations of assembling the displacement mechanism;

DETAILED DESCRIPTION

The following description of preferred embodiments of the invention is not intended to limit the invention to these preferred embodiments, but rather to enable any person skilled in the art to make and use this invention.

Device for Positioning an Electrode in Tissue

Figure 1:
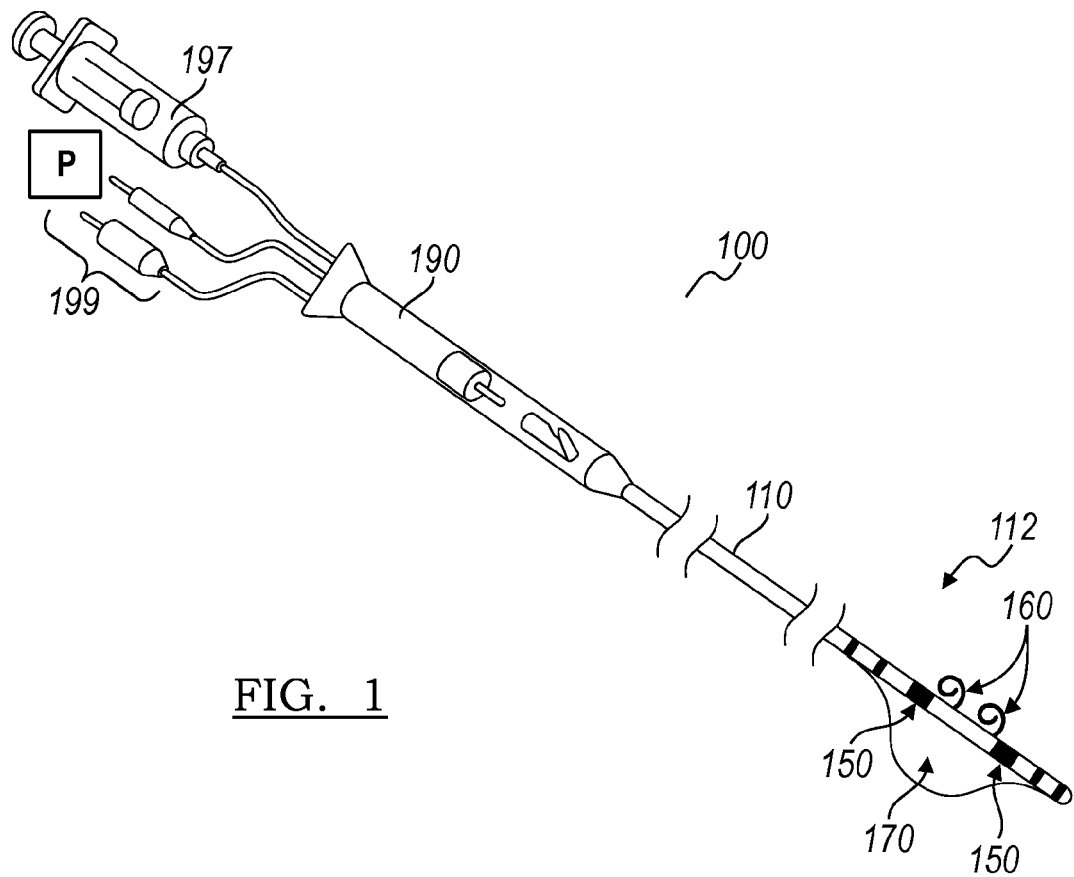
FIGS. 1 and 2 are overall and detail views, respectively, of the system of a preferred embodiment.

As shown in FIG. 1, the device 100 of a preferred embodiment for positioning an electrode in tissue includes:

an elongate lead body 110 having a distal portion 112; an electrode array 150 coupled to the distal portion of the elongate lead body; an anchoring element 160 disposed within the elongate lead body and having a distal anchor tip 162, in which the anchoring element 160 is selectively operable in a first configuration 164 in which the anchor tip is substantially retracted within the elongate lead body and in a second configuration 166 in which the anchor tip is at least partially extended outside the elongate lead body and configured to fixate within the tissue 102; and a displacement mechanism 170, coupled to the distal portion 112 of the elongate lead body 110, that is selectively expandable to bias the electrode array 150 and/or the anchoring element 160 toward the tissue 102. The device 100 may further include an actuator 140 disposed within the lead body 110 and abuttingly engaged with or otherwise coupled to the anchoring element 160 to actuate the anchoring element 160 between the first and second configurations. The device 100 may further include a handle 190 that is coupled to the elongate body and includes a slide coupled to the actuator with first and second slide positions corresponding to the first and second configurations of the anchoring element, respectively.

Figure 2:
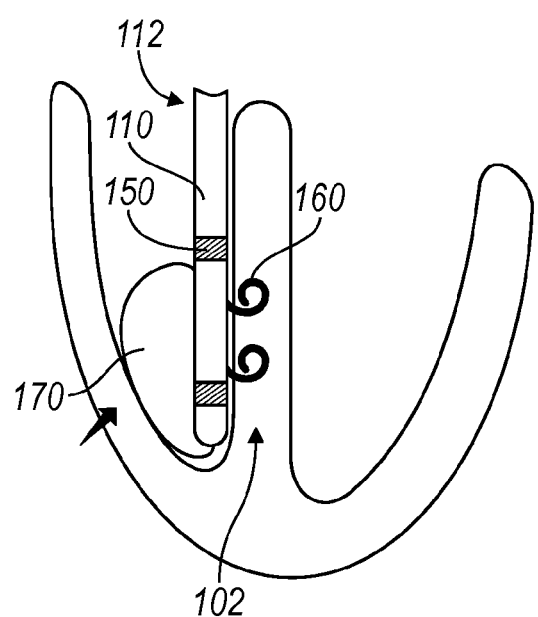

The device is preferably used to securely place a pacing electrode lead in cardiac tissue, such as for temporary bradycardia support. The device enables reliable implantation and maintenance of the position of the electrode lead. In particular, as shown in FIG. 2, the elongate body is preferably navigable through the cardiovascular system (e.g. veins, arteries) into the right ventricle of the heart, such that when the displacement mechanism 170 is expanded, the electrode array 150 and/or one or more anchoring elements 160 are biased towards the intraventricular septum. The anchoring elements 160 are configured to fixate within tissue to secure the electrode array in contact with the intraventricular septum (tissue 102), which the electrode array may stimulate to help regulate heart rate. However, the device may alternatively be used to secure any suitable electrode array in any suitable tissue. For instance, in one variation (e.g. includes the electrode array, anchoring elements and a mode of delivery such as a catheter, without including a displacement mechanism), the device may be used in applications such as laparoscopic surgery, general surgery, spinal surgery, and/or other procedures for any suitable tissue.

1.1 Lead Body

The elongate lead body 110 of the device functions to contain and deliver the electrode array 150, anchoring element 160, and displacement mechanism 170 to target tissue within the body. The elongate lead body is preferably a steerable lead or other elongate body, such as a catheter with a stylet, preformed curve, or other internal steering system. Such steering systems are known by one ordinarily skilled in the art, although the elongate body or lead may include any suitable steering system for navigating in the cardiovascular system or other portion of the body. The lead is preferably approximately cylindrical, but may alternatively be substantially flat or planar, or have any suitable cross-section. The lead is preferably flexible and made of a biocompatible material such as polyurethane or polyimide, although at least some portions may be rigid.

As shown in FIG. 3, the lead preferably includes a plurality of lumens that carry control elements (e.g. steering elements, electrical conductors 116 coupled to the electrode array 150, anchoring elements 160, actuator 140 coupled to the anchoring elements, and/or fluid channel coupled to the displacement mechanism 170). At least some of these lumens may contain internal tubing within which a control element is telescopically disposed. The lumens may be arranged in groups such as a first group including at least one lumen 132 for the actuator 140 and anchoring element 160, a second group including at least one lumen 134 for the conductors 116 (potentially including a ground wire 118), and a third group including at least one lumen 136 for the fluid or other actuator for the displacement mechanism. One or more of the lumens and/or internal tubing may be shaped with keys or other features to prevent rotation of control elements within the lead. For instance, as shown in FIG. 3C, the lumen 132 for the anchoring elements 160 may have an approximately rectangular cross-section to constrain alignment of the anchoring elements in a particular direction.

Figure 3A:
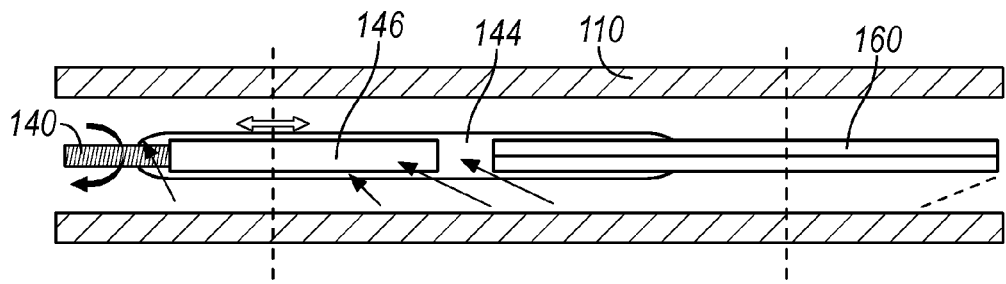
FIGS. 3A-3H are detailed views of variations of the lead body of the system of a preferred embodiment.

The first group of lumens passing along the lead preferably includes a lumen 132 for the actuator 140. The actuator 140 is preferably longitudinally translatable within the elongate body and abuttingly engaged with the anchoring element 160 to actuate the anchoring element between the first and second configurations. The actuator is preferably flexible, to help keep the overall lead body 110 flexible, such as for navigation through tissue and reduced tissue damage. In one variation, as shown in FIG. 3E, the actuator 140 includes at least a flexible portion that includes a helical cut or groove path 142 passing longitudinally along and circumferentially around the actuator. For instance, the actuator may include a wire portion disposed within or otherwise coupled to a tube portion having a helical cut 142. However, the actuator may have a series of circumferential rings, include pleats or zig-zag cuts, or any suitable cuts and/or other features to contribute to flexibility of the actuator. In another variation, the actuator is additionally and/or alternatively made of mesh or flexible material.

The first group of lumens preferably further includes a lumen 132 for the anchoring elements 160 extending from, and approximately concentric with, the lumen 132 for the actuator 140. Between the lumens for the anchoring elements and actuator, the lead preferably further includes a sleeve 144 that functions to decouple the anchoring elements from rotation of the actuator and/or lead. In a preferred variation, as shown in FIG. 3A, the sleeve is fixed to the anchoring elements 160 and not fixed to the actuator 140, such that the actuator 140 is free to rotate independently from the anchoring elements within the sleeve 144 and the actuator 140 is free to translate to abuttingly engage the anchoring elements 160. For instance, an abutting cylinder 146 coupled to the distal end of the actuator 140 is preferably configured to push and/or pull the anchoring elements 160 within the lead body 110. Alternatively, the actuator 140 may be fastened to the sleeve and the anchoring element may be not fastened to the sleeve. In further alternative variations, both the actuator and the anchoring elements may be fastened (FIG. 3D) or unfastened to the sleeve 144, or coupled to the sleeve in any suitable manner. In another alternative variation, the actuator 140 may be coupled directly to the anchoring elements 160 (e.g. crimping, welding) or be integrally formed from the same piece as the anchoring elements. The actuator 140 and/or anchoring element 160 may be fastened to the sleeve by a snap lock such as a ball joint, crimping, fasteners or adhesive.

The second group of lumens preferably includes one or more lumens 134 for the conductors 116 that carry a current and/or a ground lead 118. The conductors are preferably wires made of an electrically conductive material, but may be tubing or another elongate shape. As shown in FIG. 1, the proximal ends of the conductors are preferably coupled to generator electrodes 199 and a power source P that are external to the patient, and the distal end of the conductors are preferably coupled to the electrode array 150. In one variation, the device may include one current-carrying conductive lead per electrode in the electrode array such that each electrode can be individually controlled. In a second variation, at least a portion of the current-carrying conductors may be coupled to multiple electrodes. In a third variation, at least a portion of the current-carrying conductors may be coupled directly to an electrode, which is in turn coupled to one or more additional electrodes such that at least a portion of the current-carrying conductors is indirectly coupled to one or more electrodes. However, the device may include any suitable ratio of conductors to electrodes in the electrode array, and in any suitable arrangement.

The third group of lumens passing along the lead preferably includes one or more lumens 136 for an actuator of the displacement mechanism 170. In a preferred variation, the third group of lumens includes a lumen or channel that carries a fluid (preferably air) that may be used to expand the displacement mechanism. In this variation, as shown in FIG. 1, the proximal end of the fluid-carrying lumen may be coupled to a syringe or other pump 197 that displaces fluid through the fluid-carrying lumen 136, and the distal end of the fluid-carrying lumen may be coupled to the displacement mechanism 170. In other variations, the third group of lumens may carry wires, rods, springs or any suitable actuator for the particular kind of displacement mechanism in the device.

Figure 3B:
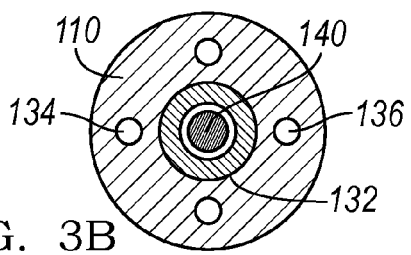
Figure 3C:
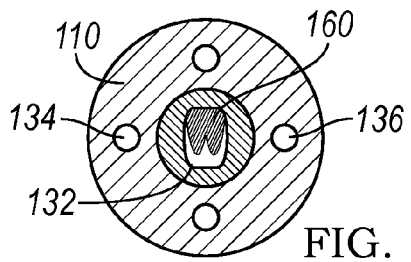
Figure 3D:
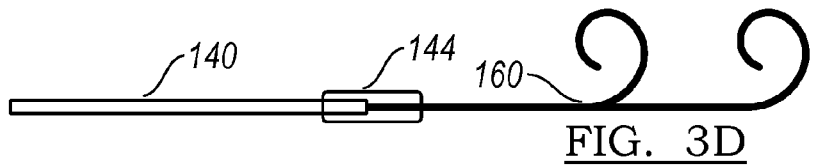
Figure 3E:
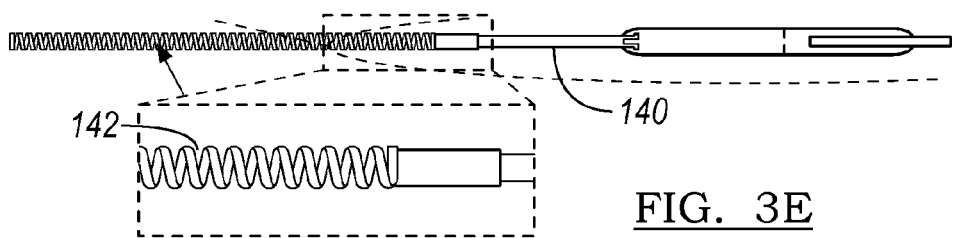
Figure 3F:
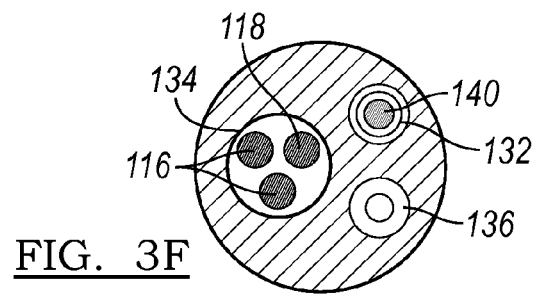

In a preferred embodiment, as shown in FIGS. 3B-3C, the first group of lumens (including a lumen for housing the actuator 140 and anchoring elements 160) is a central lumen 132 passing approximately axially along the lead body 110, and the second and third groups of lumens (housing the conductors and displacement mechanism actuator) are peripheral lumens 134 and 136 that are circumferentially distributed around the central lumen 132. Alternatively, as shown in FIG. 3F the lumen 132 for housing the actuator and anchoring elements may be off-center, and the second and/or third groups of lumens 134 and 136 may be arranged in other off-center lumens. However, any of the groups may be distributed, combined or otherwise arranged in any suitable manner.

Figure 3G:
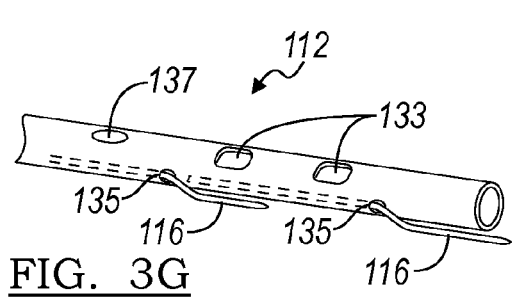
Figure 3H:
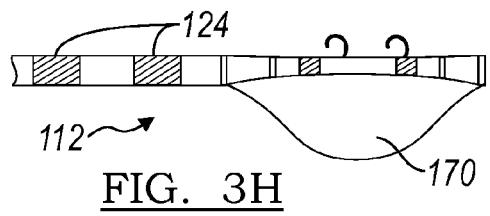

As shown in FIG. 1, the lead preferably further includes a distal portion 112 to which the electrode array 150, one or more anchoring elements 160, and one or more displacement mechanisms are coupled. As shown in FIG. 3G, the distal portion defines one or more apertures 133 through which the anchoring elements 160 deploy, preferably defining one aperture 133 per anchoring element but alternatively the ratio of apertures 133 to anchoring elements may be less than or greater than 1:1. Similarly, the distal portion 112 preferably defines one or more apertures 135 through which the conductors 116 extend to couple to the electrode array, with one aperture 135 per conductive lead, or with the ratio of apertures to conductors less than or greater than 1:1. Alternatively, the distal portions of the conductors may remain within the elongate lead body 110, and the electrode array 150 or other interconnects may extend through the apertures 135 into the elongate lead body to couple to the conductors. Similarly, the distal portion 112 preferably defines at least one aperture 137 through which air or another fluid actuates the displacement mechanism. As shown in FIG. 3H, the distal portion 112 or other portions of the lead may also include contrast markers 124 made of a material that is visible under fluoroscopy, such as to aid visual confirmation of device position or placement.

Figure 4A:
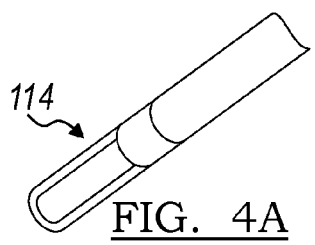
FIGS. 4A and 4B are variations of an atraumatic tip of the lead body of the system of a preferred embodiment.
Figure 4B:
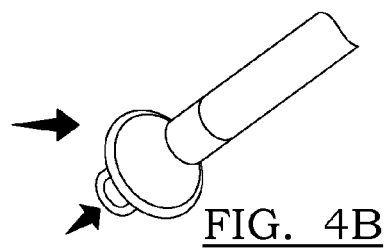
Figure 5A:
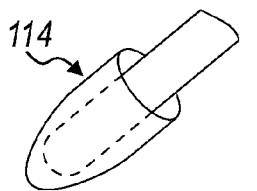
FIGS. 5A-5C are variations of an atraumatic tip of the lead body of the system of a preferred embodiment.
Figure 5B:
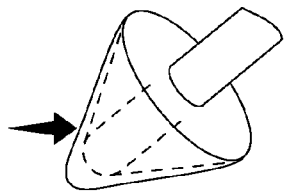
Figure 5C:
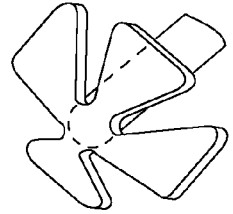
Figure 6A:
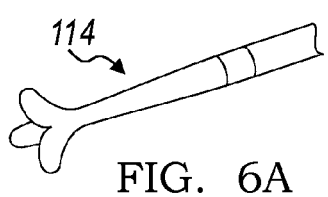
FIGS. 6A and 6B are variations of an atraumatic tip of the lead body of the system of a preferred embodiment.
Figure 6B:
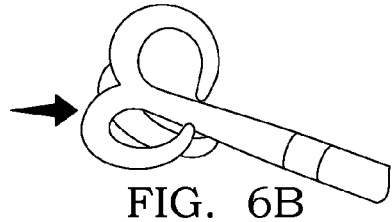
Figure 7A:
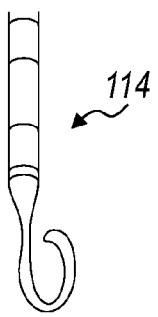
FIGS. 7A-7D are variations of an atraumatic tip of the lead body of the system of a preferred embodiment.
Figure 7B:
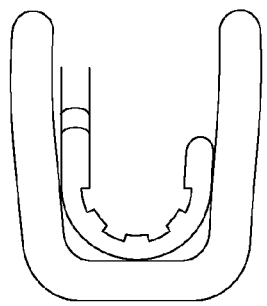
Figure 7C:
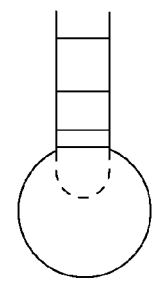
Figure 7D:
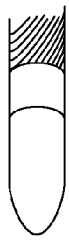

The distal portion 112 of the lead preferably further includes an atraumatic tip 114, which functions to reduce or eliminate the likelihood of perforation or other damage to the tissue as the lead is navigated through tissue. The atraumatic tip 114 absorbs at least substantially frontal forces (longitudinal force in a proximal direction), and more preferably forces in additional directions. The atraumatic tip 114 may include softer, impact-absorbing material such as elastomer with a relatively low durometer, and/or may include geometry to help absorb forces. In a preferred embodiment, as shown in FIGS. 4A and 4B, the atraumatic tip 114 includes a hollow tubular structure. The hollow tubular structure is preferably somewhat narrow and elongate in a free uncompressed mode (FIG. 4A) relative to when in a compressed mode (FIG. 4B) such as when the atraumatic tip 114 encounters the right ventricle or other tissue). When the atraumatic tip is compressed, the hollow tubular structure preferably flares radially and increases surface are potentially in contact the tissue, thereby reducing risk of performation. The atraumatic tip 114 may additionally and/or alternatively include one or more features of several variations. In a first class of variations, the atraumatic tip 114 includes other versions of an expandable tip, such as an expandable cap ("mushroom" shape) as shown in FIGS. 5A and 5B, expandable "umbrella" tines as shown in FIG. 5C, "peeling" tines as shown in FIGS. 6A and 6B or a distal balloon as shown in FIG. 7C. In a second class of variations, the atraumatic tip deforms in a curled manner upon experiencing frontal forces. In one example, as shown in FIG. 7A, the atraumatic tip may include a flexible tip that curls when experiencing frontal forces, and may further include an internal stylet that helps direct the curling of the flexible tip as the tip absorbs force. In another example, as shown in FIG. 7B, the atraumatic tip may includes notches that bias the tip to curl in a particular direction to absorb force. In a third class of variations, as shown in FIG. 7D, the atraumatic tip may include a soft, compressible material and/or have a rounded (e.g. hemispherical) or smooth shape.

Figure 8:
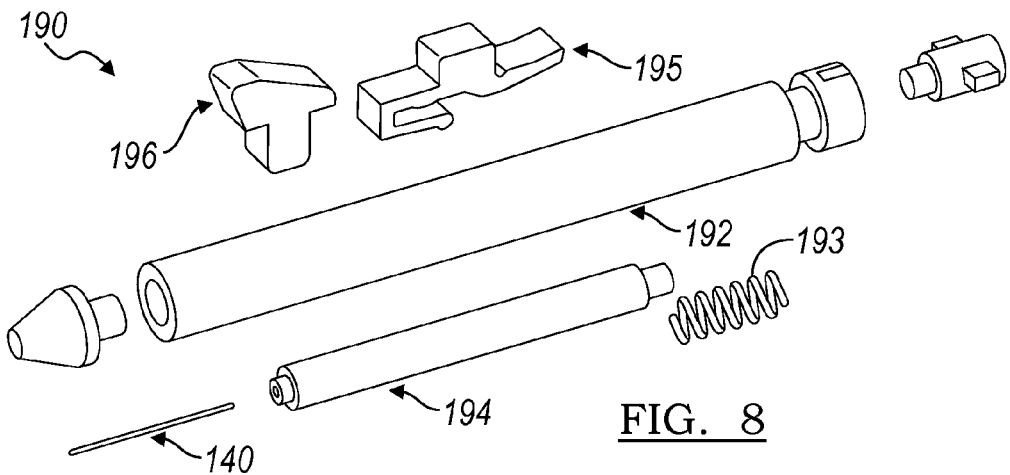
FIGS. 8 and 9A-9D are an exploded view and longitudinal cross-sectional views of operation, respectively, of the handle in the system of a preferred embodiment.
Figure 9A:
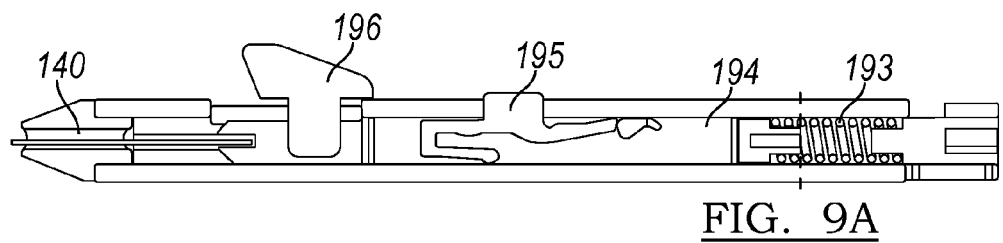
Figure 9B:
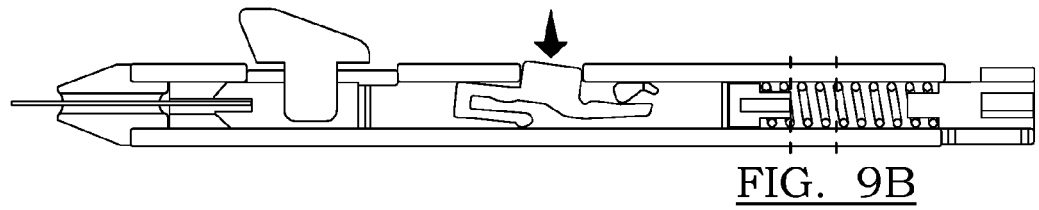
Figure 9C:
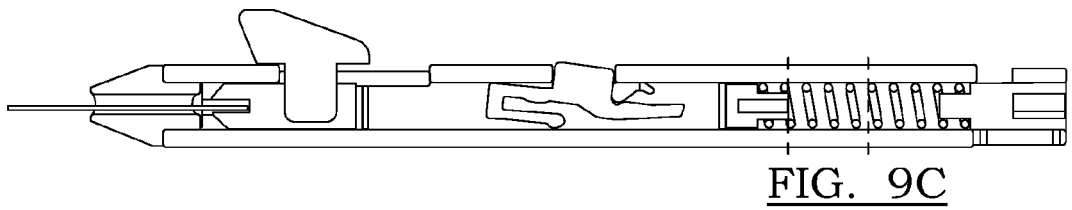
Figure 9D:
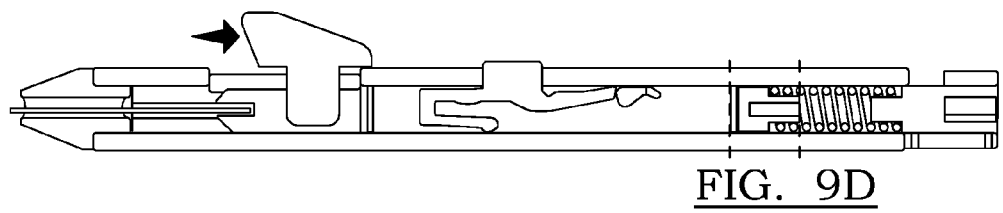

The device preferably further includes a handle 190 coupled to the lead body 110. As shown in FIG. 1, the handle is preferably coupled in-line to the lead body such that rotation of the handle corresponds to rotation of the lead body, although the handle may alternatively be coupled to the lead body 110 in any suitable manner. The handle 190 is preferably a tubular housing that contains the actuator, the conductors, and/or actuator for the displacement mechanism 170. As shown in FIGS. 8-9, the overall shape of the handle is preferably cylindrical (e.g. somewhat pen-shaped), with a tapered distal end from which the elongate lead body extends, but alternatively may be a bar-shaped handle, a cross-shape, somewhat planar, or have any suitable cross-section or overall shape. The handle 190 includes a slide 194 coupled to the actuator 140 with first and second slide positions corresponding to the first and second configurations of the anchoring element, respectively. As shown in FIG. 9A, the handle 190 further includes a trigger release 195 that selectively engages the slide 194, such that when the trigger release is engaged with the slide, the slide is constrained in the first slide position, thereby keeping the anchoring element in the second configuration. In a preferred embodiment, the slide 194 is biased (such as spring-loaded with spring 193) towards the second slide position, such that when the trigger release is disengaged from the slide (FIG. 9B), the slide is loaded to forcefully travel from the first slide position to the second slide position (FIG. 9C), thereby deploying the anchoring element from the lead body. Alternatively, when the trigger release is disengaged from the slide, the slide may be freely movable by the user between the first and second slide positions. The trigger release 195 is preferably a button that provides a first stop to prevent slide movement from the first slide position to the second position (FIG. 9A) and a second stop to prevent slide movement further distal than the second position (i.e. restrain the slide in the second position as in FIG. 9D). The handle 190 preferably further includes a reload switch 196 that retracts the slide from the second slide position to the first slide position, thereby retracting the anchoring elements into the lead body (FIG. 9D).

Figure 10A:
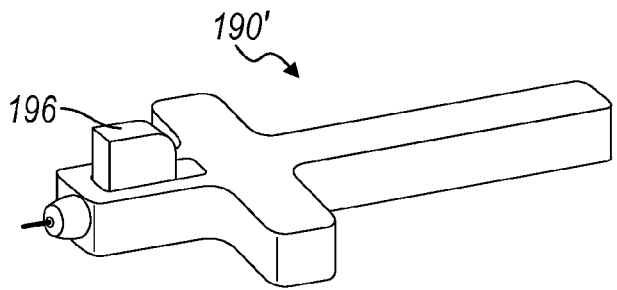
FIGS. 10A-10E are variations of the handle in the system of a preferred embodiment.
Figure 10B:
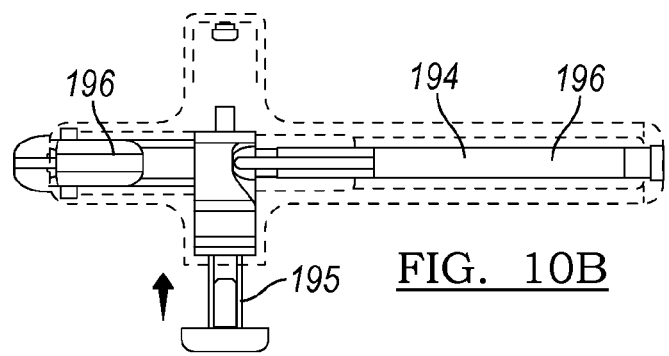
Figure 10C:
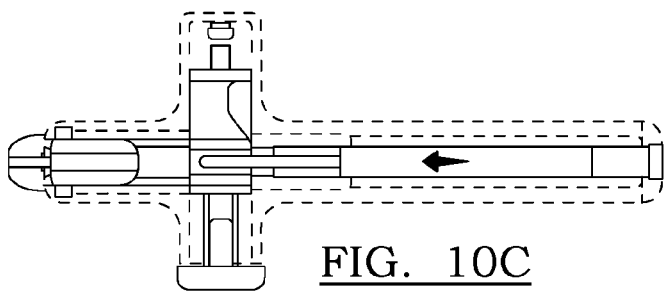
Figure 10D:
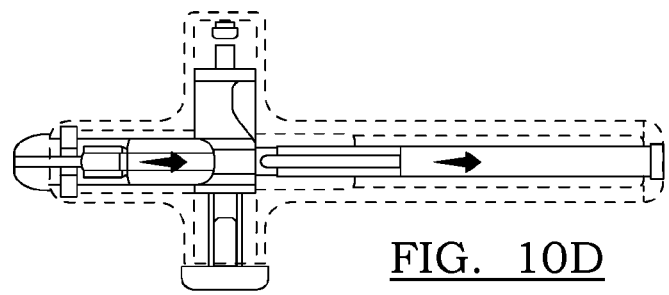
Figure 10E:
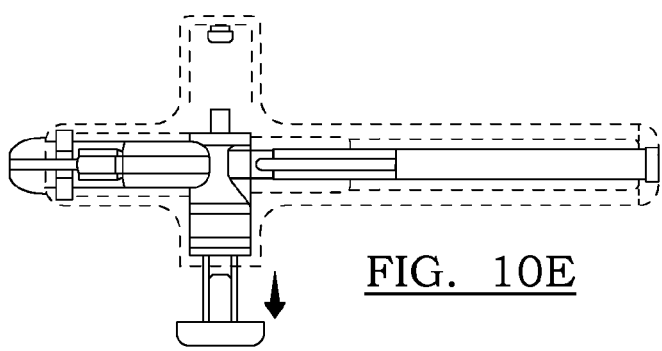

In an alternative embodiment, as shown in FIGS. 10A-10E, the handle may be a cross-shaped handle 190' in which the reload switch 196 is decoupled from the slide 194 such that when the trigger release 195 is disengaged from the slide 194 (FIG. 10B), the slide is loaded (e.g., with spring 193) to travel from the first slide position to the second slide position (FIG. 10C), without effecting corresponding movement of the reload switch 196. Similar to the preferred embodiment of the handle, the reload switch 196 retracts the slide from the second slide position to the first slide position, thereby retracting the anchoring elements into the lead body (FIG. 10D) and enabling the trigger release 195 to reengage with the slide for a repeated deployment of the anchoring elements (FIG. 10E). By default, the reload switch is in the "ready to reload" position shown in FIGS. 10B and 10C.

Figure 11:
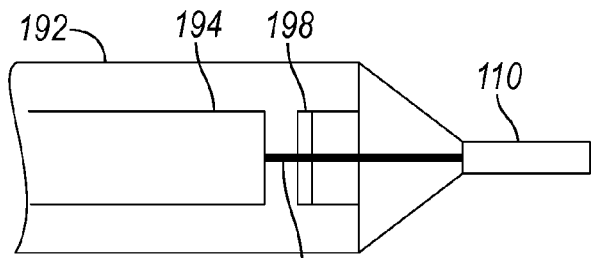
FIG. 11 is a variations of the handle in the system of a preferred embodiment.

The handle 190 may further include a septum 198 that reduces likelihood of blood and other fluids from entering the lead body 110 (e.g. through apertures of the anchoring elements 160) when the lead body is placed within the body. The septum 198 prevents a pressure gradient between inside the lead body 110 and outside environment (e.g. right ventricle), such that fluids do not travel into the lead. As shown in FIG. 11, in a preferred embodiment, the septum 198 is coupled to the tapered distal end of the handle and includes a thin membrane that the slide or actuator (e.g. wire portion of the actuator) can penetrate and travel through with little friction during anchoring element deployment and retraction. Alternatively, the septum 198 may be coupled to the inside of the lead at any location along the lead. The septum is preferably made of an elastomeric material. However, the septum may alternatively include any suitable structure and/or material that prevents a pressure difference between the inside and outside of the lead, thereby preventing fluid migration through the lumens of the lead.

Figure 12A:
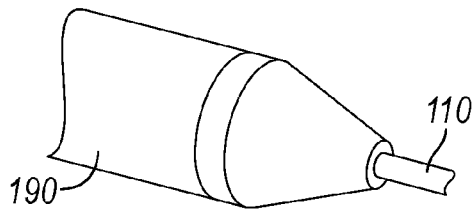
FIGS. 12A-12D are variations of the handle in the system of a preferred embodiment.
Figure 12B:
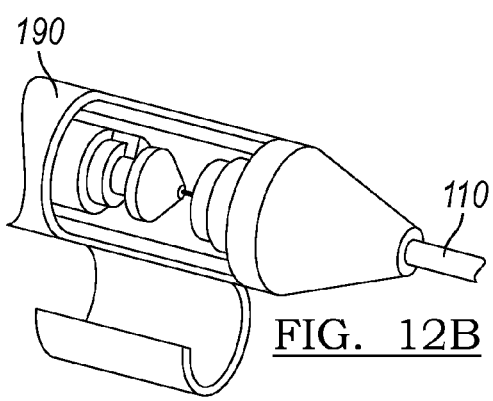
Figure 12C:
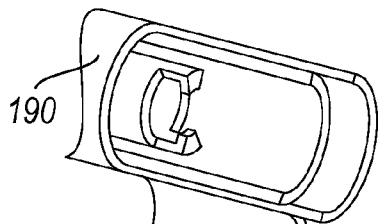
Figure 12D:
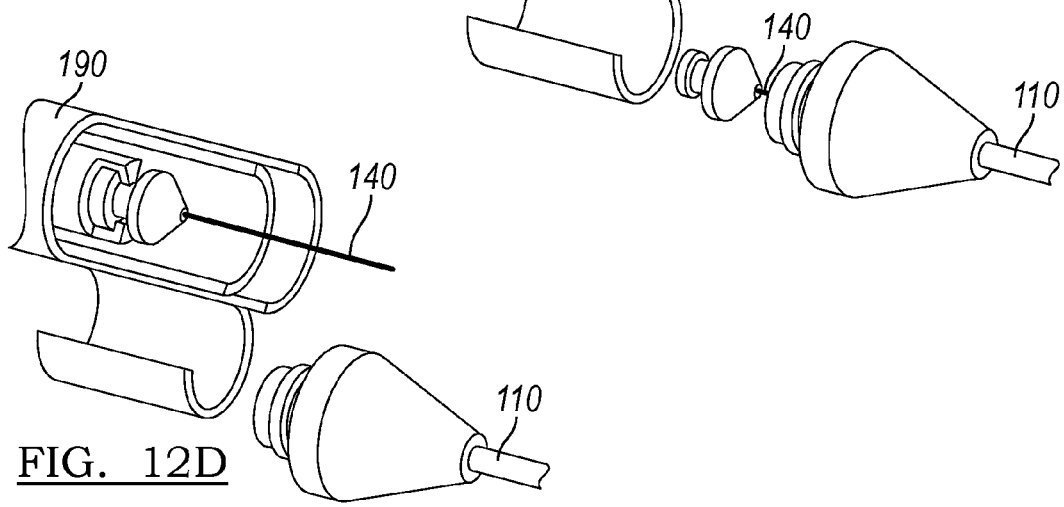

In some embodiments, the handle 190 is detachable from the lead. For instance, the handle may be detached after the anchoring elements are deployed and the electrode array 150 is fixated in the desired position. After the electrical lead has served its purpose and the anchoring elements are ready to be retracted from the tissue, the handle may be reattached to the lead. In these embodiments, the handle 190 may be a reusable tool that is sterilized and reused with multiple implantable lead devices (which may be disposable devices), although both the handle and lead may be disposable. In these embodiments, as shown in FIGS. 12A and 12B, the handle 190 may include a compartment accessible by a hinged cover and enables access to decouple particular mechanisms. In a first variation, as shown in FIG. 12C, the actuator 140 is decoupleable from the slide, thereby decoupling the lead 110 from the handle. In a second variation, the actuator 140 is decoupleable from the sleeve 144 and/or anchoring element 160, such that the handle and actuator may be pulled in a proximal direction away from the lead to decouple from the lead 110 as shown in FIG. 12D, thereby decoupling the lead from the handle. However, the handle may be detachable from the lead in any suitable manner.

Figure 13A:
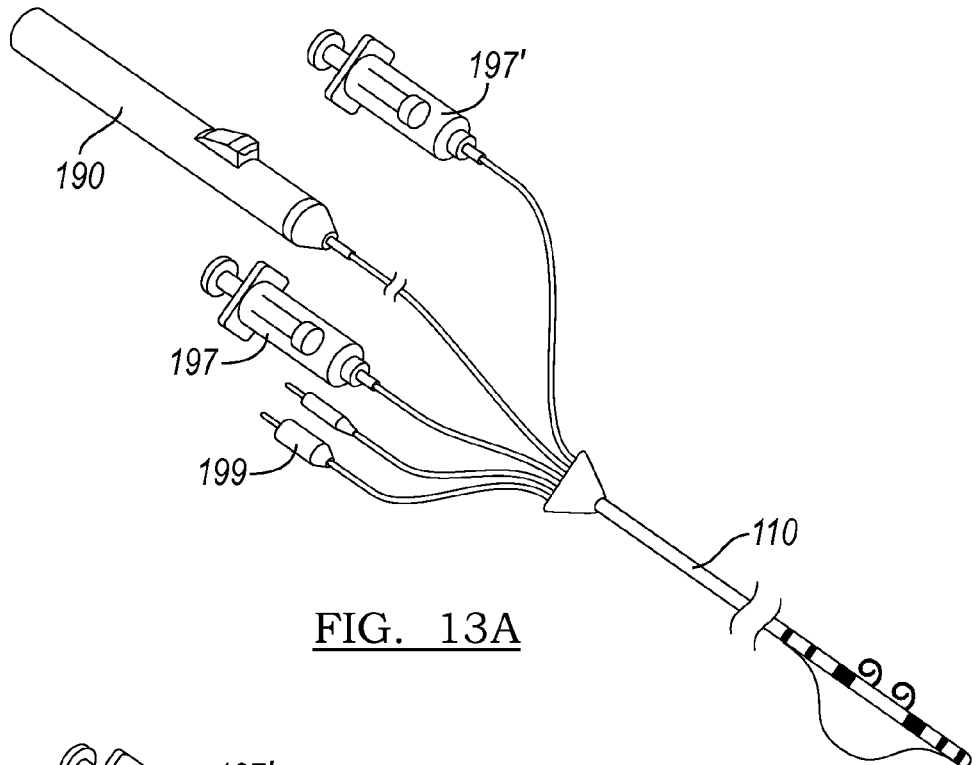
FIGS. 13A and 13B are variations of the handle in the system of a preferred embodiment.
Figure 13B:
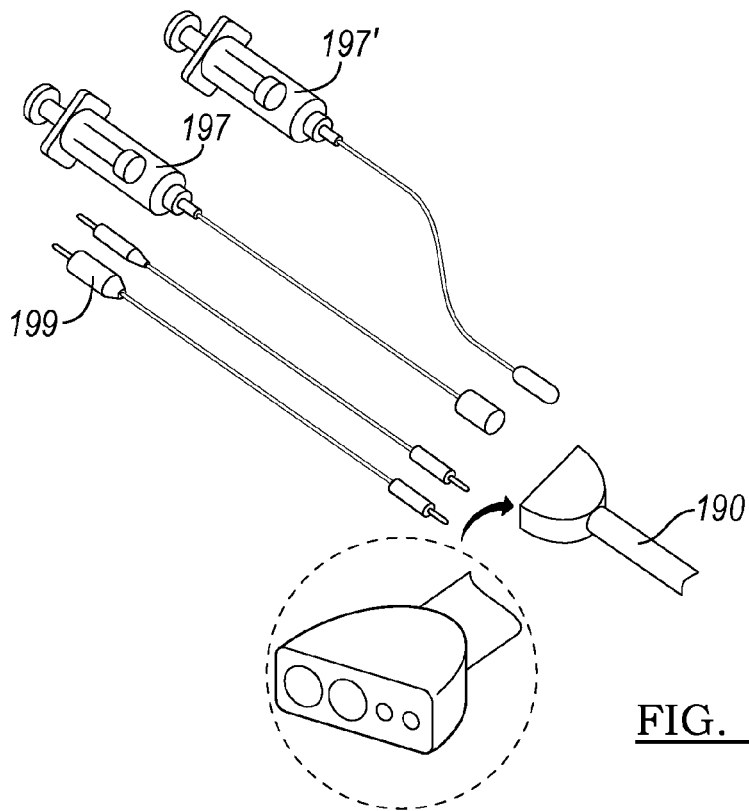

As shown in FIG. 1, generator electrodes and the fluid pump (e.g. syringe), coupled to the conductors and displacement mechanism actuator, respectively, are preferably located proximal to and aligned with the handle 190. However, as shown in FIG. 13A, in an alternative embodiment the generator electrodes, fluid pump 197 for the displacement mechanism, and/or fluid pump 197' for contrast fluid are coupled to the lead body 110 near the handle 190, such as at a junction with a Y-connector or other suitable connector. As shown in FIG. 13B, the generator electrodes 199 and/or fluid pumps 197 and 197' may be decoupled from the handle 190. For instance, the proximal end of the handle 190 may include ports that receive generator electrode plugs and fluid supply (e.g. luer lock coupling) for the displacement mechanism 170.

1.2 Electrode Array

Figure 14A:
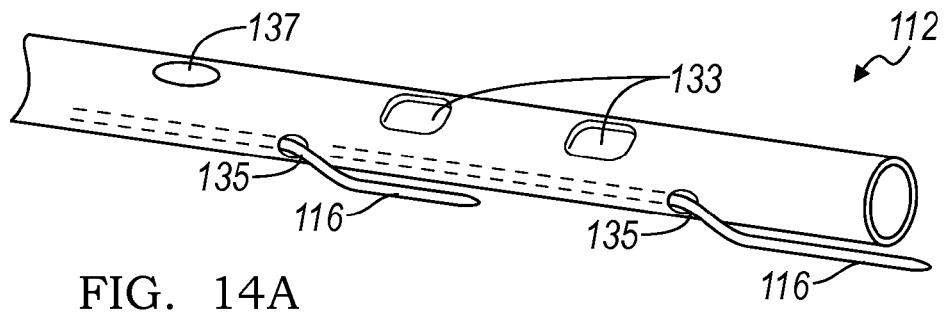
FIGS. 14A-14D are schematics of a process for assembling the electrode array in the system of a preferred embodiment.
Figure 14B:
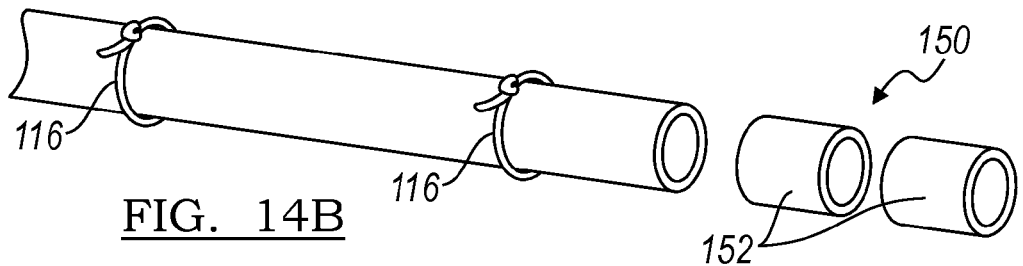
Figure 14C:
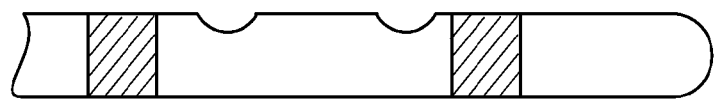
Figure 14D:
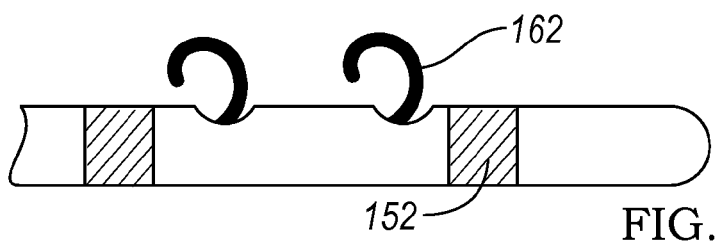
Figure 15:
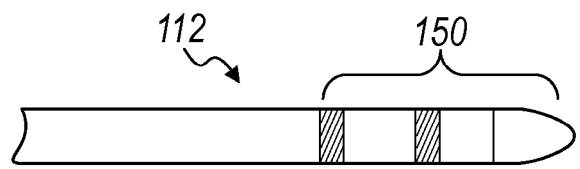
FIG. 15 is a schematic of a variation of the electrode array.

The electrode array 150 functions to provide a stimulation current to target tissue. As shown in FIG. 14, the electrode array preferably includes one or more stimulation electrodes arranged on the distal portion 112 of the lead body 110. In particular, the electrodes may be pacing electrodes for temporary support of bradycardia, but may additionally and/or alternatively be any suitable kind of electrodes. In a preferred embodiment, the electrodes are ring or bands arranged serially along the length of the lead body 110, but may additionally and/or alternatively include any suitable electrodes of other shapes (e.g planar, circular, elliptical) arranged in any suitable manner. For instance, as shown in FIG. 15, the electrode array 150 may include an electrode on the distal tip of the lead. In one preferred embodiment, the electrode array 150 includes two ring electrodes 152 arranged on the distal portion 112 of the lead body 110.

During manufacture and assembly of the device, the electrodes are placed in electrical contact with the conductors 116 that carry current along the lead body. As shown in FIG. 14A, the conductors are preferably passed along respective lumens within the lead body and extended outside the lead body through respective apertures. The extended ends of the conductors are wrapped circumferentially around the lead body, and the ring electrodes are slipped over the lead body 110 and over the wrapped conductors (FIG. 14B). The electrodes may be secured over the wrapped conductors with epoxy or crimping, and then swaged or otherwise modified until the outer diameter of the ring electrodes is substantially equal to the diameter of the lead body, such that the electrodes lie flush with the lead body. However, the electrode array and the lead may be manufactured and assembled in any suitable method.

1.3 Anchoring Element

Figures 16A, 16B:
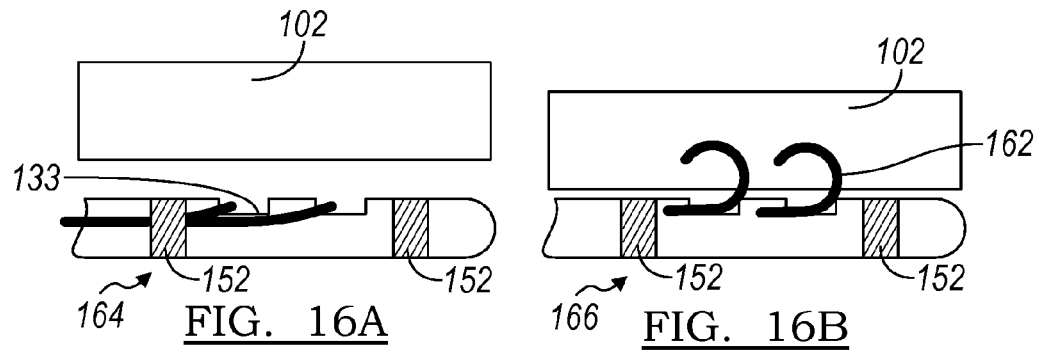
FIGS. 16A and 16B are schematics of the anchoring elements in the first and second configurations, respectively, in the system of a preferred embodiment.

The anchoring elements 160 of the device function to fixate with tissue, thereby securing the electrode array 150 adjacent to target tissue. The device may include one or multiple anchoring elements, each with an anchoring element body and an anchor tip 162. As shown in FIG. 16, the anchoring elements 160 selectively operate between a first and second configuration, where the anchoring elements are preferably operated in the first configuration 164 while the lead is navigated in tissue to the target tissue, and in the second configuration 166 when the lead is adjacent to the target tissue, although the anchoring elements may be operated in any suitable manner. In one embodiment, the first and second configurations are "deployed" and "retracted" modes, respectively, of the anchoring elements. In the first configuration 164 the anchoring element is positioned at a first anchoring element position within the lead body 110, and the anchor tip 162 is substantially refracted within the lead body (FIG. 16A). In the second configuration 166, the anchoring element is positioned at a second anchoring element position within the lead body 110 and the anchor tip 162 is at least partially extended outside the lead body and configured to fixate within tissue (FIG. 16B). The second anchoring element position is preferably distal to the first anchoring element position, such that transition from the first configuration to the second configuration corresponds to a distal movement of the anchoring element (and the actuator 140, which is preferably coupled to the anchoring elements 160). However, in other variations the transition from the first configuration to the second configuration may correspond to any other suitable kinds of movement (e.g. proximal, rotational) movement of the anchoring element.

Figures 17A, 17B, 17C:
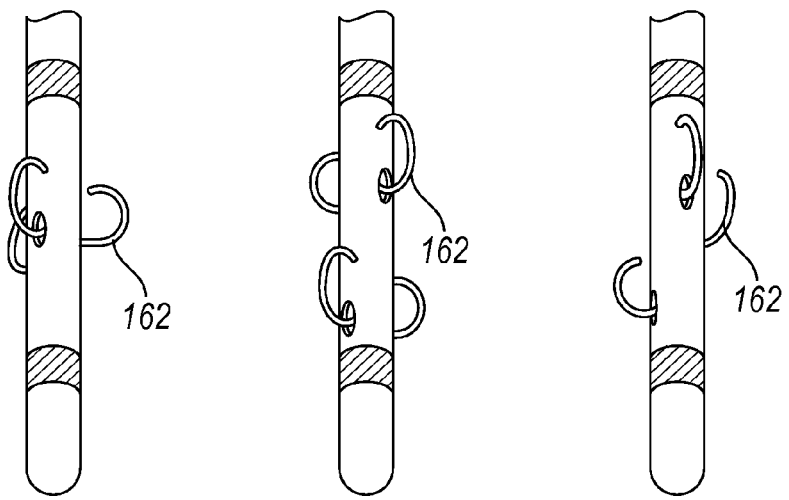
FIGS. 17A-17C are variations of the anchoring elements in the system of a preferred embodiment.
Figures 18A, 18B, 18C, 18D, 18E:
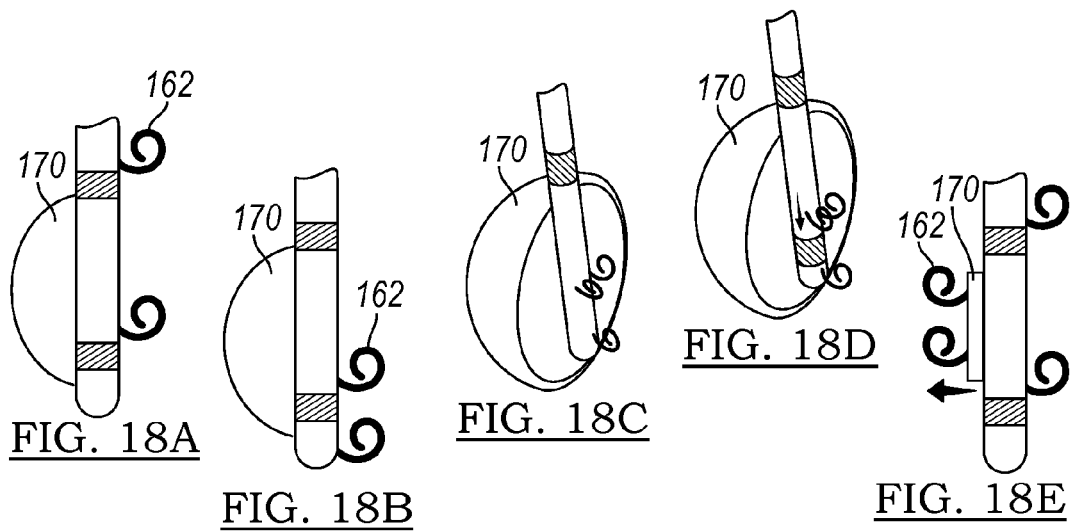
FIGS. 18A-18E are variations of the anchoring elements in the system of a preferred embodiment.

The device preferably includes a plurality of anchoring elements 160, although in some embodiments the device may includes only one anchoring element. In a first variation, the anchoring elements are longitudinally aligned such that the anchor tips deploy in approximately the same direction (FIG. 16). In a second variation, the anchoring elements are laterally aligned and circumferentially distributed around the lead body 110 (FIG. 17A). In a third variation, the anchoring elements are distributed both longitudinally along and circumferentially around the lead body 110, such as in a staggered arrangement (FIG. 17B) or spiral arrangement (FIG. 17C). Furthermore, as shown in FIGS. 18 and 19, the plurality of anchoring elements 160 may be located along the lead body 110 between electrodes, alternating with electrodes, and/or proximal and distal to electrodes (with electrodes between the anchoring elements). In a specific preferred embodiment, the device includes two anchoring elements longitudinally aligned with one another and located on the distal portion 112 of the lead body between the two ring electrodes. At least a portion of the anchoring elements may additionally and/or alternatively be coupled to a surface (e.g. outer or underside) of the displacement mechanism 170 (FIG. 18E), or on the distal tip of the lead body. However, the device may include any suitable number of anchoring elements on any suitable portion of the lead body and/or displacement mechanism or other portion of the device, which may depend on the application of the device.

Figure 19A:
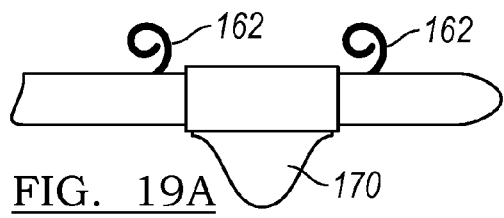
FIGS. 19A-19C are variations of the anchoring elements in the system of a preferred embodiment.
Figure 19B:
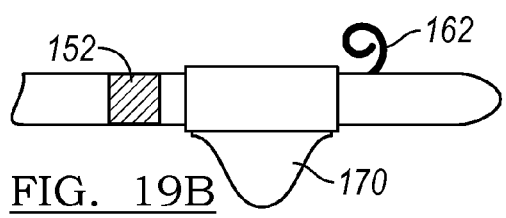
Figure 19C:
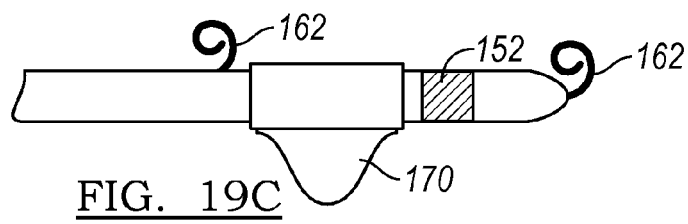

In an alternative embodiment, one or more anchoring elements 160 may additionally and/or alternatively function as an electrode to replace or supplement the functionality of the electrode array 1 50. For example, an anchoring element may include an electrically conductive alloy or other material such as tantalum, where the anchoring element is wholly made of, embedded with, or coated with the electrically conductive material. This alternative embodiment of the device may include various relative positions of anchoring elements, electrodes, and the displacement mechanism. For example, as shown in FIG. 19A, the lead body 110 may include anchoring elements 160 (functioning as electrodes) proximal and/or distal to the displacement mechanism 170, without additional, separate electrodes. As shown in FIGS. 19B and 19C, the lead body 110 may include both an anchoring element functioning as an electrode, a separate ring electrode, and/or an anchoring element on the distal tip of the lead body.

Figure 20A:
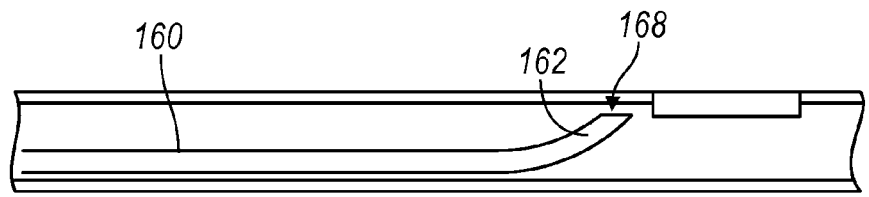
FIGS. 20A-20D are variations of the anchoring elements in the system of a preferred embodiment.
Figure 20B:
Figure 20C:
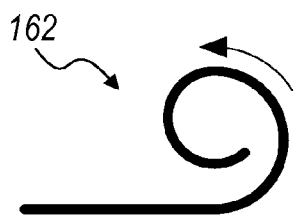
Figure 20D:

The anchor tip 162 of an anchoring element is preferably uncurled in the first configuration, located within a lumen of the lead body 110. As shown in FIG. 20A, the anchor tip 162 preferably has a biased cut 168 forming a sharpened point, with the bias cut angled such that when the anchor tip is retracted within the lead body 110, the cut is substantially parallel to the wall of the lumen and may smoothly slide along the wall to reduce the friction between the anchor tip and the wall of the surrounding lumen and reduce force requirements for deployment. However, the bias cut may be angled at any suitable angle. In one embodiment, when transitioning to the second configuration, the anchor tip 162 preferably curls upon itself in at least a partial loop (e.g. partially circular loop such as "U"-shaped or "J"-shaped, or partial loop of other shapes such as triangle or square), such that after the sharpened point pierces the tissue, further deployment of the anchoring element results in the anchor tip burrowing and fixating in a curled manner. The curled shape or state helps reduce shifting or dislodgement of the anchor tip in that it is resistant to forces in many directions. As shown in FIG. 20B, in the second configuration the anchor tip 162 is preferably curled in a circular loop having uniform radius of curvature, although as shown in FIG. 20C, alternatively the radius of curvature may vary (e.g. spiral inwards). The anchor tip 162 may curl or bend in such a manner as to cross or overlap with itself. The anchor tip 162 may also bend in such a manner as to trace a path that returns toward the lead body, such as to contact the external portion of the lead body and/or re-enter the lead body. Retraction of the anchoring element after deployment withdraws the curled anchor tip in a reverse direction in the path that it burrowed during deployment and restores the anchor tip in a straightened shape within the lead body. In a preferred embodiment, uncurled refers to the relative configuration of the anchor tip 162 when substantially retracted within the elongate body. Curled refers to the relative configuration of the anchor tip 162 when at least partially extended outside the elongate body. The shape of the anchor tip 162 in the first and second configurations may be of one or more of several variations, although it may be any suitable shape. In alternative variations, as shown in FIG. 20D, the anchor tip may additionally and/or alternatively include hooks, barbs (e.g. acute bends) or other fixation features in any suitable shape. Furthermore, the anchor tip 162 may include bioresorbable material such that after a certain amount of time, the anchor tip dissolves and is absorbed into the body, and/or may include material that promotes or prevents tissue adhesion. The anchoring elements 160 are preferably made of nitinol wire or other biocompatible shape memory alloy, but may alternatively be formed wire and/or coated with any suitable biocompatible material. In an alternative variation, the anchoring elements may be of variable stiffness along the length, such as by allowing gel infusion into selected portions of the anchoring element or conducting an electrical signal to electrically-sensitive material to vary rigidity.

The anchoring elements 160 are preferably deployed and retracted, as described above, by spring-loaded or manually controlled longitudinal movement of the actuator within the lead body 110. However, in another variation, the anchor tips may be coupled to the displacement mechanism 170, such that when the displacement mechanism expands, the anchor tips are deployed and fixated within the tissue. In other variations, the anchoring elements may be actuated with any suitable mechanism, such as cords. Furthermore, the deployment and retraction of the anchoring elements may be triggered by a manual action specifically for the anchoring elements (e.g. button or slide on the handle 190) and/or automatic means (e.g. triggered by expansion or unexpansion of the displacement mechanism or based on existence of electrical contact between the anchoring element and the electrode array).

The device preferably further includes one or more mechanisms for verifying anchoring element deployment and fixation in tissue, which may additionally and/or alternatively be modified for verifying anchoring element retraction and removal from tissue (such as before removal of the lead from the patient). Furthermore, the anchor deployment verification mechanism may further function to verify the position of the electrode array 150 relative to tissue. As shown in FIG. 21, in one variation, the anchor deployment verification mechanism includes a fluid injection port in the lead body that enables release of fluoroscopic contrast fluid under fluoroscopy. For example, the apertures from which the anchoring elements deploy may enable contrast fluid 122 to flow out of the lead. When the anchoring elements 160 are not fixated in tissue, the released contrast fluid will at least initially tend to diffuse in approximately the same direction as the anchoring element deployment (FIG. 21A). When the anchoring elements 160 are fixated in tissue, the released contrast fluid flow will initially be blocked by the tissue and flow away from the tissue (FIG. 22B). Monitoring the flow of contrast fluid and/or using the contrast fluid to visualize the target environment (e.g., right ventricle) under fluoroscopy aids visual confirmation of anchor tip fixation in tissue 102. The contrast fluid injection may be manually controlled such as with syringe 197' and/or automatically triggered by another action, such as deployment of anchoring elements.

Another variation of the anchor deployment verification mechanism includes an electrical feedback circuit including one or more of the anchoring elements and one or more electrodes in the electrode array 150. As shown in FIG. 22A, when a deployed anchor tip is not properly fixated in tissue, contact between the deployed anchor tip and a nearby electrode on the lead body triggers a switch on the electrical feedback circuit that is used to signal the error in anchor tip fixation. As shown in FIG. 22B, when the deployed anchor tip is properly fixated in tissue, the tissue prevents contact between the deployed anchor tip and the electrode and leaves the switch open, which is used to signal correct anchor tip fixation. Implementation of this switch to an external electrical system is known and readily understood by one ordinarily skilled in the art.

As shown in FIG. 23, another variation of the anchor deployment verification mechanism includes at least two sets of electrical pad pairs on the lead body 110, including: a distal pad pair 128d near and on the same side as the anchoring elements 160 and electrodes and configured to contact the tissue, and a proximal pad pair 128p on an opposite side of the anchoring elements 160 and configured to face away from the tissue. The electrical pad pairs provide outputs of Vd (voltage output across the distal pad pair) and Vp (voltage output across the proximal pad pair). When the anchor tips are not properly fixated and the electrodes are not in contact with the tissue, Vd=Vp (approximately) because both electrical pad pairs are in contact with the same environment (e.g. blood, but not in contact with tissue). When the anchor tips are properly fixated and the electrodes are in contact with the tissue, Vd>Vp due to the impedance of the tissue in contact with the distal pad pair. The ratio between Vd and Vp (or the absolute or relative difference between Vd and Vp) can be displayed on a real-time graph, or other display such as an LED display or LCD screen, to the user operating the device in a patient, such that the change in the ratio results in a change in the displayed signal and, when the signal difference surpasses a particular threshold, the signal indicates tissue contact with the distal electrical pad pair 128d, anchor tips 162, and electrode array 150.

Another variation of the anchor deployment verification mechanism includes pressure sensors. In one version, as shown in FIG. 24, a pressure sensor 126 is coupled to the lead body 110 and senses when the tissue is in contact when the lead body. In other versions, the pressure sensor may be coupled to the anchoring element, the electrode array 150, or any suitable portion of the device. Furthermore, although the anchor deployment verification mechanism is preferably one or more of these variations, the mechanism may additionally and/or alternatively be any suitable mechanism.

1.4 Displacement Mechanism

The displacement mechanism 170 functions to bias the electrode array 150 and/or anchoring elements, or other portion of the lead body, in a particular direction, preferably toward the tissue. As shown in FIGS. 21-24, the displacement mechanism is preferably coupled at least partially circumferentially around the distal portion of the lead body 110, and more preferably on at least a side of the lead body opposite the electrode array and/or anchoring elements. The displacement mechanism may additionally and/or alternatively be coupled to the lead body on the same side as the anchoring elements (e.g. the anchoring elements 160 may be coupled to the outer side of the displacement mechanism 170), or circumferentially offset from the anchoring elements by approximately 90 degrees (FIG. 25A) or any other suitable angle. The displacement mechanism 170 may be selectively unexpandable to reverse the bias of the electrode array 150 and/or anchoring elements 160, such as after the deployment and fixation of the anchoring elements in the tissue. The device preferably includes one displacement mechanism 170, but may include multiple displacement mechanisms arranged on the lead body in any suitable arrangement; for example, as shown in FIG. 25B, the device may include a proximal displacement mechanism 170 located proximal to the electrode array and anchoring elements, and a distal displacement mechanism 170' located distal to the electrode array and anchoring elements.

Figure 26A:
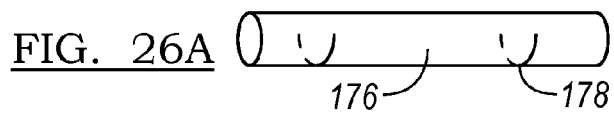

The displacement mechanism 170 preferably includes a balloon 172 that is selectively inflatable through a fluid channel in the lead body 100. The balloon is preferably made of an elastomeric material such as silicon or polyurethane, but may alternatively be made of any suitable material. As shown in FIG. 26, in a preferred embodiment the balloon may include circumferential bands 174 that slip over the lead and are sealed to couple the balloon to the lead. A preferred method of manufacture of the displacement mechanism includes cutting two partially circumferential slits 178 along the length of a tube 176 (FIG. 26A), folding the central portion between the slits inwards to form two circumferential bands 174 at each end of the tube (FIG. 26B), sliding the distal portion of the lead body 110 into the circumferential band, and sealing the edges of the tube to the lead body (FIG. 26C). The lead body preferably includes an aperture 137, located underneath with a portion of the balloon, that provides air or other fluid to inflate the balloon 172 (FIG. 26D). Alternatively, the balloon may be constructed from sheets. At least two sheets 180 may be sealed together face-to-face around their periphery to form an inflatable volume that is coupled to the lead body 110 and has an aperture aligned with an aperture in the lead body, such that air or other fluid in the fluid channel in the lead body passes through the apertures of the lead body and inflatable volume to expand the inflatable volume. In a first variation, as shown in FIG. 27A, the inflatable volume is made from rectangular sheets and bonded to a tubular band that slips over and couples to the distal portion 112 of the lead body, and the tubular band 182 has an aperture that aligns with the other apertures to enable expansion of the inflatable volume. In a second variation, as shown in FIG. 27B, the inflatable volume is made of sheets with one or more extensions 184 (e.g. "I"-shaped, "H-shaped", "E"-shaped or "L"-shaped sheets) that are wrapped around the lead body to form the circumferential bands. In an alternative embodiment, the balloon is an approximately spherical or spheroidal volume, or another kind of inflatable volume that is coupled to the fluid channel of the lead body.

In alternative variations, the displacement mechanism 170 may be other expandable mechanisms, such as an expandable and retractable ring, scaffold, or coil. In some embodiments, the device may further include a mechanism for verifying displacement mechanism expansion and/or retraction. For instance, the displacement mechanism may include contrast markers to visually aid confirmation of displacement mechanism expansion/retraction under fluoroscopy. In other variations, the mechanism for verifying displacement mechanism expansion/retraction may be similar to the anchor deployment verification mechanism.

Alternative embodiments of the device 100 may include any combination of the variations of the lead body, handle, electrode array, anchoring element, displacement device, and other mechanisms described above, and may include additional suitable variations of such mechanisms and other suitable modifications.

Example of an Embodiment of the Device

Figure 28A:
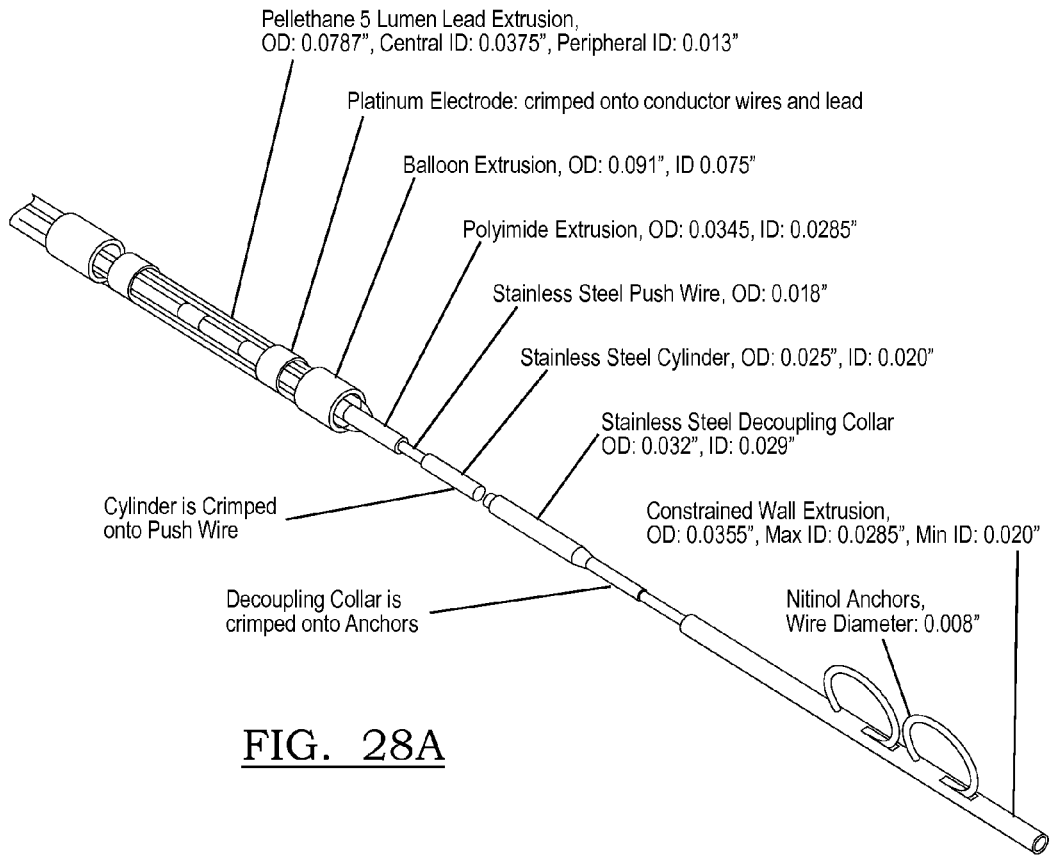
FIGS. 28A and 28B are schematics of an example of the system of a preferred embodiment.
Figure 28B:
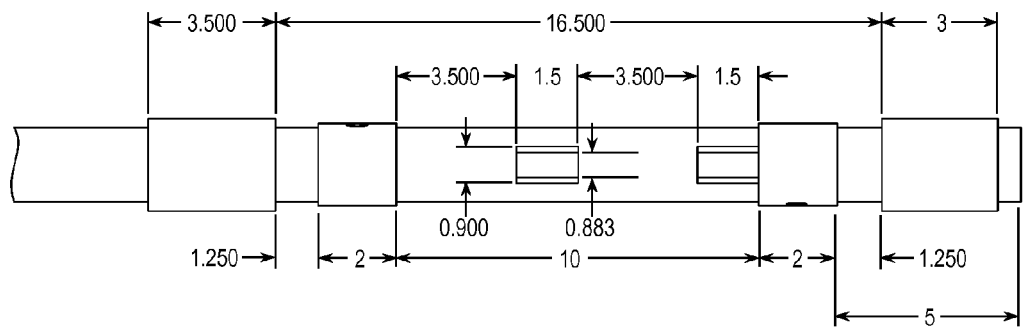

In an example of an embodiment of the device, the device includes a handle, an elongate tubular pellethane lead body distally coupled to the handle and having a distal portion that defines a plurality of apertures, including two conductive lead apertures, two anchoring element apertures, and an air aperture. As shown in FIGS. 28A and 28B, coupled to the distal portion of the lead body are: two stimulating electrodes suitable for pacing cardiac rhythm, two nitinol anchoring elements with anchor tips that selectively deploy out of the lead body through respective anchoring element apertures, and an inflatable balloon coupled to the lead body on a side opposite the anchoring element apertures. The lead has an atraumatic tip including soft, compressible material. The two stimulating electrodes are platinum ring electrodes located approximately 10 mm apart. The two anchoring element apertures, which are approximately 1.5 mm long, are located between the electrodes, with the proximal anchoring element aperture located approximately 3.5 mm distal to the proximal electrode, and the distal anchoring element aperture located approximately 3.5 mm distal to the proximal anchoring element aperture. The inflatable balloon, which is approximately 16.5 mm long and selectively inflatable to bias the distal portion of the lead body in a particular direction toward tissue, is made from silicon tubing and includes two circumferential bands and a central portion between the bands. The proximal circumferential band of the balloon is approximately 3.5 mm long and is located approximately 1.25 mm proximal to the proximal electrode, and includes an aperture fluidically coupled to an air supply. The distal circumferential band of the balloon is approximately 3 mm long and located approximately 1.25 mm distal to the distal electrode. Each anchoring element is made of 0.008 in diameter nitinol wire and selectively operates in a retracted mode and in a deployed mode. The anchor tips of the anchoring elements are coated with a radio-opaque material visualizable under fluoroscopy. In the retracted mode, each anchoring element is at a proximal position in the lead body and the anchor tip is uncurled and sheathed within the lead body. In the deployed mode, each anchoring element is at a distal position in the lead body and the anchor tip is in a curled loop configured to fixate within the tissue.

The lead body defines a plurality of lumens, including a lumen receiving an actuator (stainless steel push wire with an outside diameter of 0.018 in and crimped to a stainless steel cylindrical tube with an outside diameter of 0.025 in and inside diameter of 0.020") that pushes the anchoring elements in a distal direction to deploy the anchor tips, at least two lumens each for receiving a conductive lead that extend laterally outside the lead body and couple to respective ring electrodes, and a lumen for carrying fluid to inflate the balloon. The actuator includes a sleeve or collar (stainless steel tube with an outside diameter of 0.032 in and inside diameter of 0.029 in) that is coupled to the anchoring elements, but decoupled from the actuator. Additional dimensions of the lead body are shown in FIGS. 28A and 28B.

The handle is pen-shaped and includes a trigger release button that is coupled to a spring-loaded slide that, when released, transitions the anchoring elements from the retracted mode to the deployed mode. When the trigger release is freed, the slide slides from a proximal slide position to a distal slide position corresponding to the retracted mode and deployed modes, respectively, of the anchoring elements. The spring-loaded slide enables the actuator to push the anchoring elements from the proximal position to the distal position, thereby launching the anchor tips into the curled, deployed position. The handle further includes a reload switch that retracts the slide from the second slide position to the first slide position. The handle is distally removably coupled to an air supply (syringe) that provides air for inflating the balloon, and further distally removably coupled to generator electrodes that provide current to the electrodes.

Method for Positioning an Electrode in Tissue

As shown in FIGS. 29A-29F, the method 200 for positioning an electrode in tissue in a body includes: navigating, to a location adjacent to the tissue, an elongate lead body with an electrode array, at least one anchoring element with a distal anchor tip, and a displacement mechanism S210, biasing the electrode array and/or at least one anchoring element towards the tissue with the displacement mechanism S220, deploying at least one anchoring element S230 and allowing the anchor tip to fixate within the tissue S240. The method may further include verifying position of the electrode array relative to the tissue S250 and verifying fixation of the anchor tip within the tissue S260. In a preferred embodiment, the method 200 is used to provide temporary pacing guidance from pacing electrodes in support of bradycardia, although the method may alternatively be used in any suitable electrode application. In an alternative embodiment, the method includes the step of biasing the electrode array and/or at least one anchoring element towards the tissue by deploying at least one anchoring element.

Figure 29A:
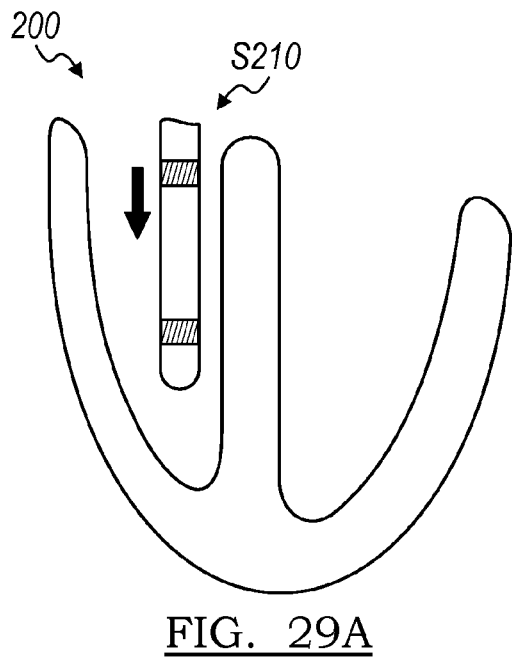
FIGS. 29A-29F are schematics of the method of positioning an electrode in tissue of a preferred embodiment.

Navigating the lead body to the tissue S210 is a step known to one ordinarily skilled in the art, and may include steps such as manipulating a handle coupled to the lead, manipulating a stylet, and activating steering wires. However, any suitable steps may be performed, depending on the exact design of the lead body (e.g. steerable lead, pre-formed curve, stylet) and/or applications of the lead in varying embodiments. Navigation may utilize fluoroscope, ultrasound, or other visual modalities. In the preferred embodiment, as shown in FIG. 29A, navigating the lead body includes navigating the lead body through blood vessels towards the heart.

Figure 29B:
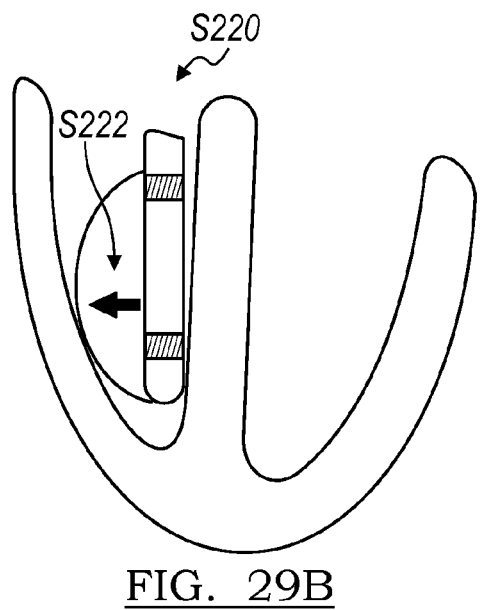

Biasing the electrode array and/or at least one anchoring element towards the tissue S220 functions to encourage direct contact between the electrode array and/or anchoring elements and the tissue, which improves fixation of the anchoring element within the tissue. As shown in FIG. 29B, biasing the electrode array preferably includes expanding the displacement mechanism S222. In a preferred variation, expanding the displacement mechanism includes inflating a balloon, such as with a syringe, pump, or manual actuation. The balloon may be on a side of the lead body opposing the anchoring elements such that the balloon pushes against a wall opposing the tissue (e.g. wall of the right ventricle opposing the interventricular septum) to displace the lead body (along with the electrode array and anchoring elements) towards the tissue. In other words, expanding the displacement mechanism includes expanding the displacement mechanism substantially opposite the direction of anchoring element deployment. In other alternative variations, biasing the electrode array and/or at least one anchoring element towards the tissue includes expanding a ring, scaffold, coil, or other suitable expanding mechanism in any suitable direction.

Figure 29C:
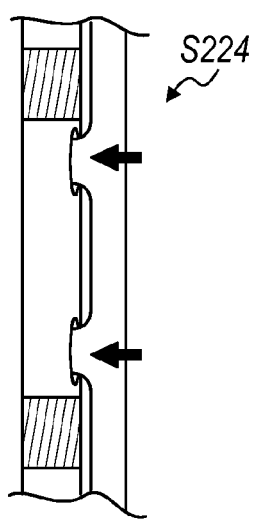

In some embodiments, as shown in FIG. 29C, biasing the electrode array and/or at least one anchoring element towards the tissue additionally and/or alternatively includes biasing the tissue towards the lead body S224. For instance, biasing the tissue towards the lead body may include applying suction to pull the tissue towards the lead body (e.g. into the anchoring element apertures or other apertures), or providing pressure on the backside of the tissue (e.g. left ventricle side of the interventricular septum).

Figure 29D:
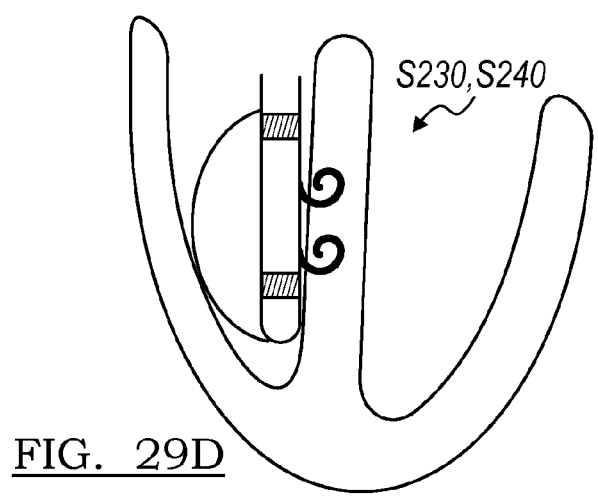

As shown in FIG. 29D, deploying at least one anchoring element S230 and allowing the anchor tip to fixate within the tissue S240 function to secure the electrode array in contact with the tissue. Deploying the anchoring element preferably includes freeing a trigger release, such as a button or slider, that releases a spring-loaded actuator to actuate the anchoring elements from the first configuration to the second configuration. However, the actuator may be actuated with a stylet, cords, or any suitable mechanism. Furthermore, in alternative variations, deploying the anchoring element may include any suitable actuation step that transitions the anchoring element from the first configuration to the second configuration. Allowing the anchor tip to fixate within the tissue preferably includes allowing the anchor tip to curl into a loop within the tissue, or additionally and/or alternatively includes allowing the anchor tip to engage barbs, hooks, or other fixation features within the tissue.

Figure 29E:
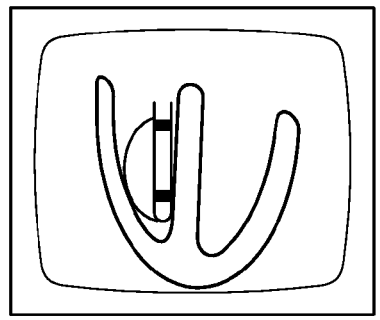
Figure 29E:
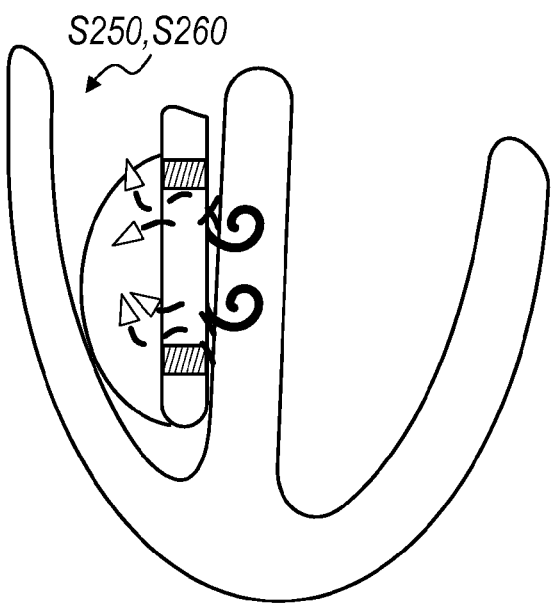

As shown in FIG. 29E, verifying position of the electrode array relative to the tissue and verifying fixation of the anchor tip within the tissue function to confirm location of the electrode array (and potentially other portions of the lead body). These verifying steps may additionally and/or alternatively function to confirm proper secure deployment of the anchoring elements within the tissue. In a first variation, verifying steps S250 and S260 include monitoring location of contrast markers coupled to at least a portion of the lead body (lead, electrode array, anchoring elements or displacement mechanism) under fluoroscopy, such as monitoring a display that provides visualization of the contrast markers under fluoroscopy. In a second variation, as shown in FIGURE verifying steps S250 and S260 include releasing contrast fluid and monitoring for obstructed path of the contrast flow under fluoroscopy. In a third variation, verifying steps S250 and S260 include receiving an electrical signal that signifies when the anchoring element is in the second configuration and fixated in the tissue. In a fourth variation, verifying steps S250 and S260 include measuring a first electrical measure (e.g. voltage, impedance) across a first set of contact points intended to be in contact with the tissue, measuring a second electrical measure across second contact points intended to not be in contact with the tissue, and monitoring a comparison between the first and second electrical measures. However, any combination of these or other suitable verifying steps may be performed.

Figure 29F:
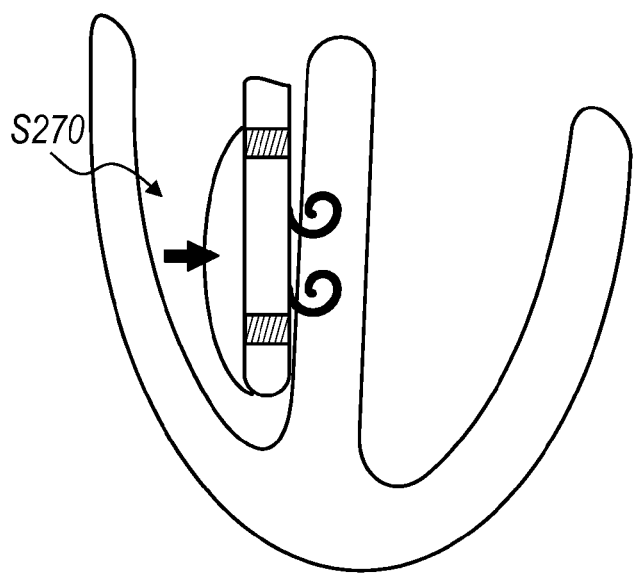

As shown in FIG. 29F, the method may further include unexpanding (e.g., retracting) the displacement mechanism S270 after allowing the anchor tip to fixate within the tissue. Unexpanding the displacement mechanism functions to substantially restore normal operation of the tissue (e.g. reducing occlusion in the right ventricle while the electrode array is coupled to the interventricular septum) and/or to enable withdrawal of the lead body from the tissue (e.g. through the cardiovascular system). Unexpanding the displacement mechanism preferably includes deflating the balloon displacement mechanism. Deflating the balloon may include withdrawing fluid from the balloon by suction (e.g. withdrawal of the syringe, reverse pump or manual actuation), or otherwise releasing fluid from the balloon (e.g. allowing a leak), although other embodiments include any suitable reverse actuation performed in expanding the displacement mechanism.

As a person skilled in the art will recognize from the previous detailed description and from the figures and claims, modifications and changes can be made to the preferred embodiments of the invention without departing from the scope of this invention defined in the following claims.

What is claimed is:

1. A method for positioning an electrode in a patient's right ventricle, said method comprising:

navigating an elongate body having a distal portion and a proximal portion to position an electrode array and at least one anchoring element carried on a side of the distal portion of the elongate body adjacent to a target tissue within the right ventricle, wherein the distal portion of the elongate body has an atraumatic tip formed from a soft, compressible material to reduce or eliminate the likelihood of perforation of the tissue as the elongate body is being navigated;

after the distal portion of the elongate body has been positioned in the right ventricle, actuating a displacement mechanism attached to a side of the distal portion of the elongate body opposite to the side which carries the electrode array and the at least one anchoring element to engage the distal portion but not the proximal portion of the elongate body against the target tissue to contact the electrode array and the at least one anchoring element against the target tissue within the right ventricle;

after actuating the displacement mechanism to engage the distal portion of the elongate body against the target tissue, deploying the at least one anchoring element on the side of the distal portion of the elongate body to affix the at least one anchoring element to the target tissue; and after deploying the at least one anchoring element, verifying fixation of the at least one anchoring element to the target tissue.

2. The method of claim 1, wherein actuating the displacement mechanism includes expanding the displacement mechanism in a direction substantially opposite to a direction of anchoring element deployment.

3. The method of claim 2, wherein the displacement mechanism pushes against a wall within the right ventricle which opposes the target tissue.

4. The method of claim 3, wherein the target tissue is on an interventricular septum and displacement mechanism pushes against a wall opposite to the interventricular septum.

5. The method of claim 2, wherein actuating the displacement mechanism includes inflating a balloon.

6. The method of claim 5, wherein the balloon is inflated against a heart wall opposite to an interventricular septum.

7. The method of claim 1, wherein the displacement mechanism applies suction to an interventricular septum.

8. The method of claim 1, wherein verifying fixation of the at least one anchoring element to the target tissue includes releasing contrast fluid and viewing the contrast fluid flow under fluoroscopy.

9. The method of claim, 1 wherein verifying fixation of the at least one anchoring element to the target tissue includes receiving an electrical signal that signifies when the anchoring element is in the second configuration and affixed to the tissue.

10. The method of claim 1, wherein verifying fixation of the at least one anchoring element to the target tissue includes measuring impedance across distal contact points intended to be in contact with the target tissue.

11. The method of claim 1, further comprising verifying a position of the electrode array relative to the target tissue.

12. The method of claim 11, further comprising deactivating the displacement mechanism after verifying the position of the electrode array, wherein the at least one anchoring element remains affixed to the target tissue after the displacement mechanism is actuated.

13. The method of claim 1, wherein the at least one anchoring element is deployed while the displacement mechanism remains actuated and the at least one anchoring element remains in contact with the target tissue.

\* \* \* \* \*